(12) United States Patent
Sherwinter

(10) Patent No.: US 10,448,939 B2
(45) Date of Patent: Oct. 22, 2019

(54) FASCIAL CLOSURE DEVICE

(71) Applicant: BRAINCHILD SURGICAL DEVICES LLC, Brooklyn, NY (US)

(72) Inventor: Danny A. Sherwinter, Brooklyn, NY (US)

(*) Notice: Subject to any disclaimer, the term of this patent is extended or adjusted under 35 U.S.C. 154(b) by 0 days.

(21) Appl. No.: 15/590,589

(22) Filed: May 9, 2017

(65) Prior Publication Data

US 2017/0238914 A1    Aug. 24, 2017

Related U.S. Application Data

(63) Continuation-in-part of application No. 14/503,648, filed on Oct. 1, 2014, now Pat. No. 9,861,356.

(51) Int. Cl.
  *A61B 17/04* (2006.01)
  *A61B 17/00* (2006.01)
  (Continued)

(52) U.S. Cl.
  CPC ...... *A61B 17/0057* (2013.01); *A61B 17/0482* (2013.01); *A61B 17/06109* (2013.01); *A61B 17/3474* (2013.01); *A61B 90/37* (2016.02); *A61B 2017/0042* (2013.01); *A61B 2017/00115* (2013.01); *A61B 2017/00637* (2013.01); *A61B 2017/00663* (2013.01);
  (Continued)

(58) Field of Classification Search
  CPC ........ A61B 17/0482; A61B 2017/0042; A61B 2017/06042; A61B 17/04; A61B 17/34; A61B 17/0485; A61B 17/0483; A61B 17/0469; A61B 17/3403; A61B 17/3423; A61B 2017/00663; A61B 2017/0474

USPC ........................................................ 606/148
See application file for complete search history.

(56) References Cited

U.S. PATENT DOCUMENTS 6,428,549 B1    8/2002 Kontos
2005/0149065 A1    7/2005 Modesitt
(Continued)

FOREIGN PATENT DOCUMENTS

WO    2007050941 A1    5/2007

OTHER PUBLICATIONS

Canadian Office Action, dated Jul. 28, 2017, for Application 2,928,615.
(Continued)

*Primary Examiner* — George J Ulsh
(74) *Attorney, Agent, or Firm* — Kilpatrick Townsend & Stockton LLP

(57) ABSTRACT

Embodiments include systems and methods for closure of a hole or other defect, for example in context of a laparoscopic surgical procedure. For example, a suturing device and method of use involve inserting the device into a hole, positioning material around the hole into a notch of the device, passing a needle through a cavity in the device and the material positioned in the notch, passing a suture through the eye of the needle, and removing the needle from the material with the suture. The suture can be removed and the process can be repeated with another end of the suture at another location through the material, around the hole. When the suture is passed through the second point of penetration, the suture can now extend both into and out of the material at different points around the hole and can be tied, thereby closing the hole.

19 Claims, 31 Drawing Sheets

(51) Int. Cl.
    *A61B 17/06*     (2006.01)
    *A61B 17/34*     (2006.01)
    *A61B 90/00*     (2016.01)
(52) U.S. Cl.
    CPC .............. *A61B 2017/00929* (2013.01); *A61B 2017/06042* (2013.01); *A61B 2090/08021* (2016.02)

(56) References Cited

U.S. PATENT DOCUMENTS

| | | |
|---|---|---|
| 2005/0165416 A1 | 7/2005 | Bojarski et al. |
| 2007/0129735 A1 | 6/2007 | Filipi et al. |
| 2008/0045980 A1 | 2/2008 | Schwarz |
| 2011/0144440 A1* | 6/2011 | Cropper .............. A61B 17/3421 600/203 |
| 2016/0095589 A1 | 4/2016 | Sherwinter |

OTHER PUBLICATIONS

Notice of Allowance for Canadian application No. 2,928,615 dated Mar. 13, 2018, 4 pages.
International Search Report and Written Opinion for PCT/US2017/031783 dated Feb. 12, 2018, 14 pages.

\* cited by examiner

FASCIAL CLOSURE DEVICE

FIELD

Some embodiments relate to surgical implements, and, more particularly, to systems and methods for fascial suturing, for example, during laparoscopic surgical procedures.

BACKGROUND

In standard surgical practice, and, specifically in minimally invasive surgical procedures, incisions (sometimes called "defects") are made in the skin, subcutaneous fat, fascia, and muscle tissue. Using standard surgical techniques, instruments are introduced through these defects to perform surgery. For example, in a laparoscopic procedure, a defect can provide a port for insertion of a trocar, which can be used for various purposes, including draining fluid and introducing laparoscopic hand instruments, cameras, etc. These defects must be closed, usually with sutures, at the conclusion of a procedure, to prevent herniation and other complications at these sites.

Some conventional techniques used to close tissue defects (or, alternatively, to close any hole where one has ready and/or direct access only to one side thereof) involve use of curved needles. Some techniques involve placing a suture through the fascia, then grasping the suture extending freely in the air within a cavity (e.g., under camera guidance). This task can be extremely difficult even in experienced hands. Further, such techniques often rely on costly specialized equipment for each procedure which is unacceptable to hospitals and surgery centers. Even with such specialized tools, surgeons typically still must rely solely on feeling their way through a cavity, and/or looking in a camera, while at the same time, risking injury to bowels, blood vessels, or other intra-abdominal organs. Small mistakes in positioning and/or use of instruments can lead to sepsis, hemorrhage, and even death. The current methods are cumbersome and require a significant learning curve for a practitioner to become proficient in the techniques.

BRIEF SUMMARY

Among other things, embodiments provide novel systems and methods for closing fascial defects, for example, in context of laparoscopic surgical procedures. For example, a novel fascial closure device is described having a closure guide for direct suturing to ensure adequate closure while avoiding injury to intra-abdominal contents. Embodiments include suturing devices and methods that can be used for suturing tissue defects, or, for suturing and closing any other hole or portal where one has direct access only to one side thereof. The structure of the fascial closure device can allow the device to be manipulated easily and accurately. Embodiments of the fascial closure device include a closed housing for an inserted needle, which can prevent the needle's sharp tip from being freely situated in the abdominal cavity.

Various embodiments include additional features. For example, some embodiments are arranged for insertion into a defect according to an oblique angle, which can assist in moving the device through tissue, fat, and fascial layers without excessive force by the user and can assist in grasping of the layers for proper closure. Other embodiments include a needle guide that can help ensure proper rotational orientation of a surgical needle in the device to facilitate intra-cavity threading of a suture through the needle eye. Other embodiments include a suture releasement through which a suture can be removed from the fascial closure device without removing the fascial closure device from the defect (e.g., to facilitate insertion of multiple sutures in a single defect without removing the fascial closure device each time).

BRIEF DESCRIPTION OF THE DRAWINGS

The present disclosure is described in conjunction with the appended figures.

In the appended figures, similar components and/or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

DETAILED DESCRIPTION

Embodiments of the disclosed technology include a safe, low cost, easy-to-use suturing device (referred to herein as a suturing device, suturing kit, fascial closure device, or the like) and technique for use thereof. The suturing device and method can be used for suturing tissue defects, or, for suturing and closing any other hole or portal where one has direct access only to one side thereof. The structure of the suturing device allows the device to be manipulated easily and accurately. Embodiments of the suturing device include a closed housing for an inserted needle, which prevents the needle's sharp tip from being freely situated in the abdominal cavity.

Embodiments of the disclosed technology will become clearer when reviewed in connection with the description of the figures herein below. In the following description, numerous specific details are set forth to provide a thorough understanding of the present invention. However, one having ordinary skill in the art should recognize that the invention may be practiced without these specific details. In some instances, circuits, structures, and techniques have not been shown in detail to avoid obscuring the present invention.

Figure 1:
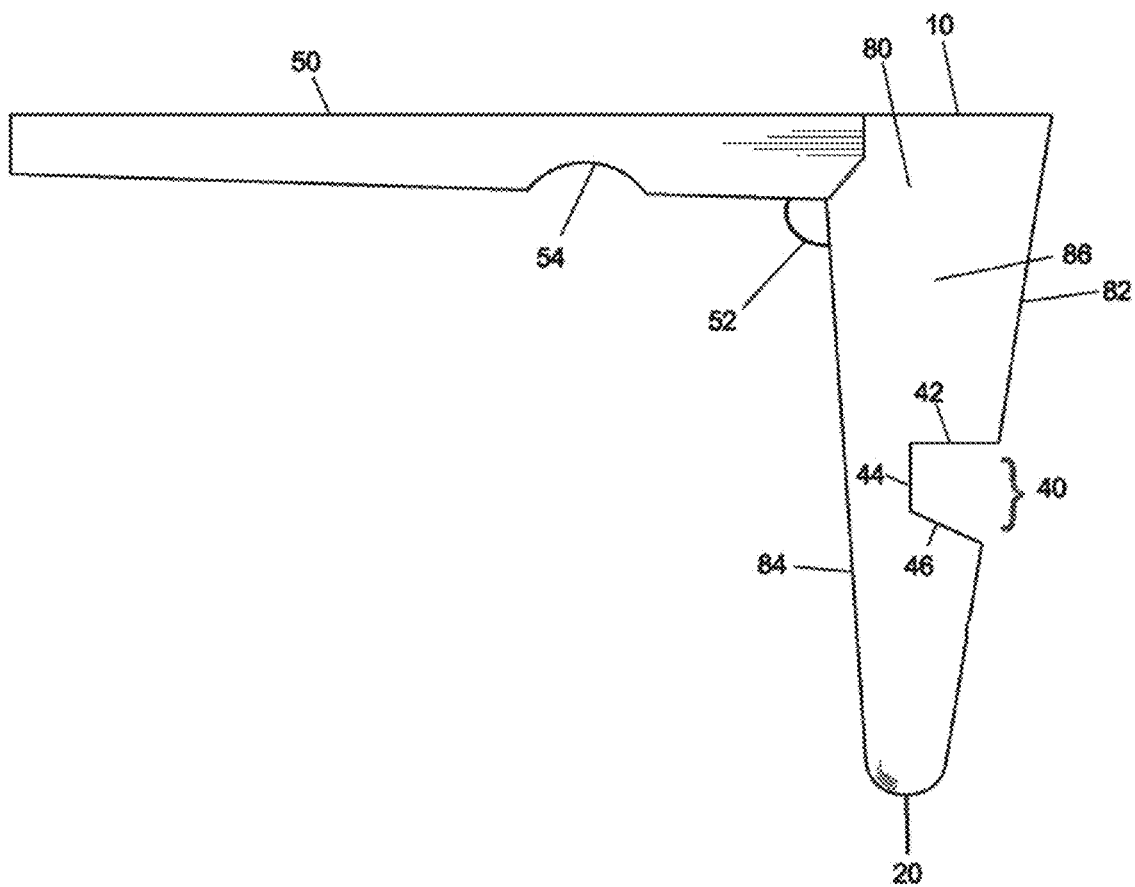
FIG. 1 shows a side elevation view of a suturing device in an embodiment of the disclosed technology.

FIG. 1 shows a side elevation view of a suturing device of embodiments of the disclosed technology. The suturing device of this embodiment is an elliptical cone 80 having a base 10 at a first end and an apex 20 at a second, opposite, end. FIG. 1 shows a side 86 of the elliptical cone. The term "elliptical cone" is defined herein as a geometric cone with a notch cut into a part thereof. The elliptical cone may be elongated in one dimension, such that the base is in the shape of an oval. In an alternative embodiment, any elongated member may be used.

A notch 40 is cut into a front side 82 (the front side 82 is opposite the side 84 adjacent to the handle) of the elliptical cone 80, the notch 40 also extending partially into adjacent and opposing sides 86, and partially between the base 10 and the apex 20 of the elliptical cone. The term "cut into" is defined as "preformed" or "removed from the described mathematically defined structure" and defines a part of a device which is lacking from the otherwise described structure. The construction thereof need not actually be "cut" from the structure after it is produced, but rather can be produced with the lack of the portion described as being "cut into" such a shape. While the notch 40 is cut into the front side 82 in this embodiment, the notch 40 can be cut into any side of the elliptical cone 80 and still be in the scope of the disclosed technology.

The notch has a top surface 42 which defines a region of the elliptical cone between the base 10 and notch 40. The notch has a bottom surface 46 which defines a region of the elliptical cone between the apex 20 and the notch 40. A back surface 44 of the notch forms the back side thereof can be substantially parallel, in embodiments of the disclosed technology, to the adjacent side 84 opposite the notch of the cone region. A continuous plane or surface is formed between the apex 20, base 10 (circumscribed also by back side 84), and back surface 44 of the notch. Still further, the bottom surface 46 may for an acute or obtuse angle relative to the back surface 44 and/or the adjacent side 84 which helps ease removal of the device from the hole being sewn.

Figure 2:
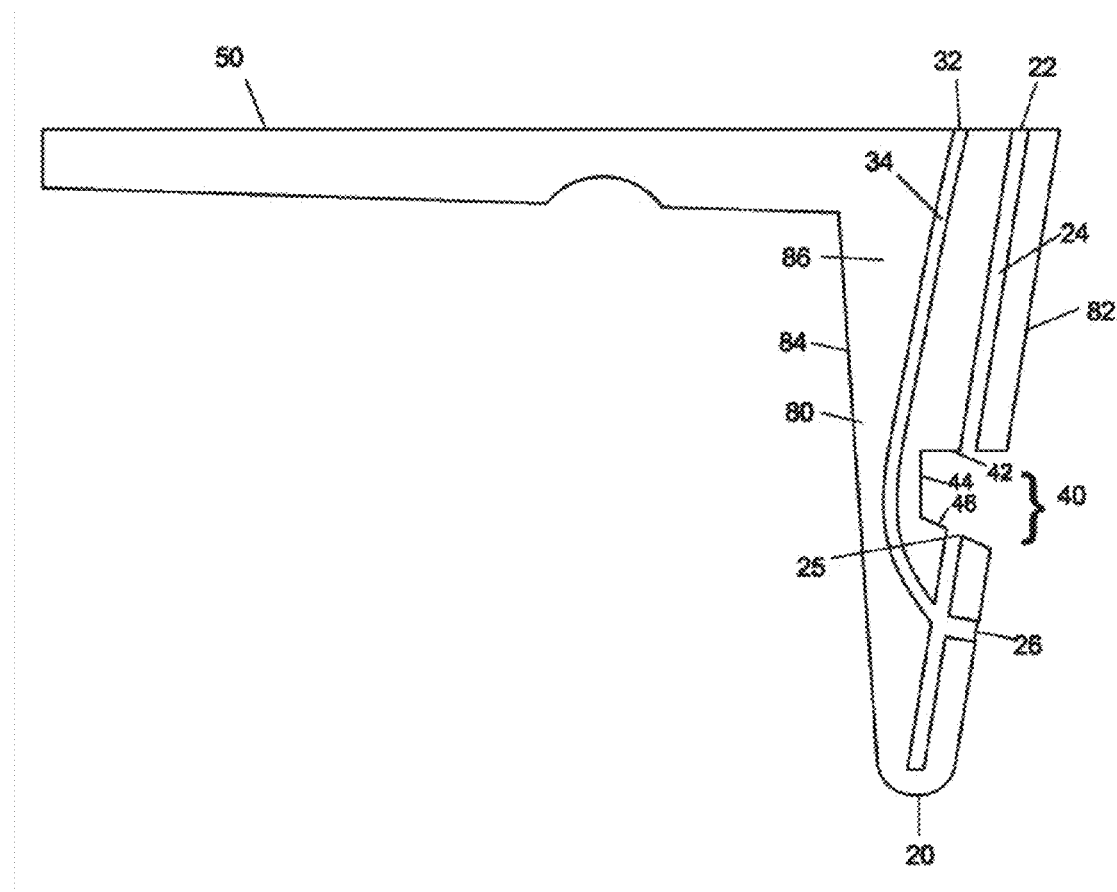
FIG. 2 shows a cutaway view of the side elevation view of the suturing device shown in FIG. 1.
Figure 8:
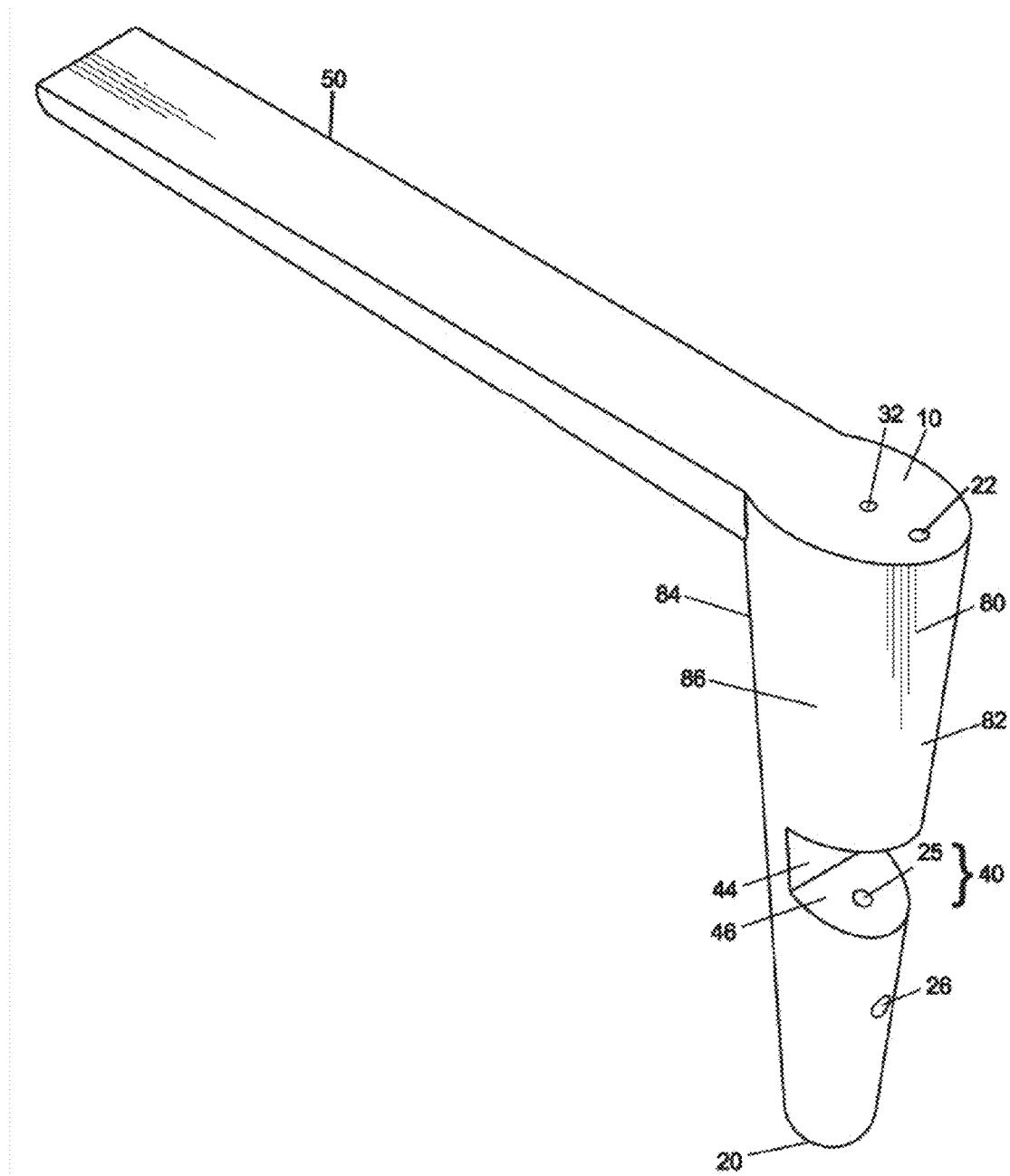
FIG. 8 shows a top and front side perspective view of a suturing device, in an embodiment of the disclosed technology.

FIG. 2 shows a cutaway view of the side elevation view of the suturing device shown in FIG. 1. FIG. 8 shows a top and front side perspective view of a suturing device in an embodiment of the disclosed technology. Now discussing FIGS. 2 and 8 simultaneously, a needle guide cavity 24 and a suture guide cavity 34 extend into the body of the elliptical cone 80. In embodiments, the needle guide cavity 24 extends in a straight path from a needle guide portal 22 at the base 10 of the elliptical cone 80, and through the body of the cone 80. The needle guide cavity 24 is then interrupted by the notch 40, after which it continues through a second needle guide portal 25 located on the bottom side 46 of the notch 40, and continues through the cone 80 towards the apex 20.

An exit portal 26 is situated on the front side 82 of the elliptical cone, between the notch 40 and the apex 20 of the cone 80. The exit portal 26 may be on side of the device, including at the apex thereof. The exit portal 26 extends substantially perpendicular from the needle guide cavity 24 at a point between the second needle guide portal 25 and a point of termination of the needle guide cavity. The needle guide cavity 24 terminates, in some embodiments, at a point before the apex 20.

The suture guide cavity 34 extends between a suture guide portal 32 located at the base 10 of the elliptical cone, and a point located between the notch 40 and the exit portal 26 of the elliptical cone 80. The suture guide portal 32 can be located substantially at the base 10, defined as located closer to the base 10 than the apex 20 of the suturing device, or, alternatively, the suture guide portal 32 may be located exactly at the base 10 of the suturing device. As shown in FIG. 2, the suture guide cavity 34 is curved and joins the needle guide cavity 24 at a point between the bottom side 46 of the notch 40 and the exit portal 26. The suture guide cavity 34 joins with, and forms a unitary cavity with, the exit portal 26 via the needle guide cavity 24.

Figure 3:
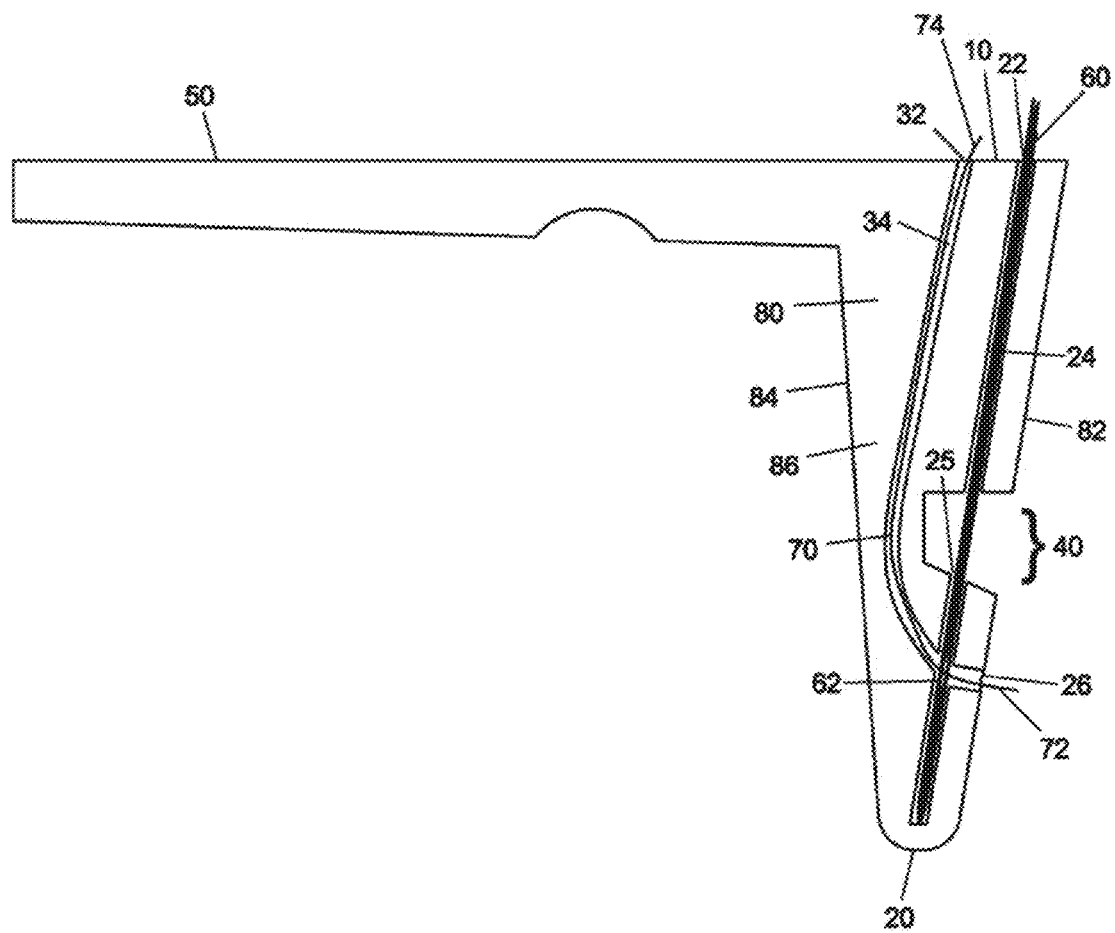
FIG. 3 shows a cutaway side elevation view of a suturing device with a needle and a suture inserted therein, in an embodiment of the disclosed technology.
Figure 9:
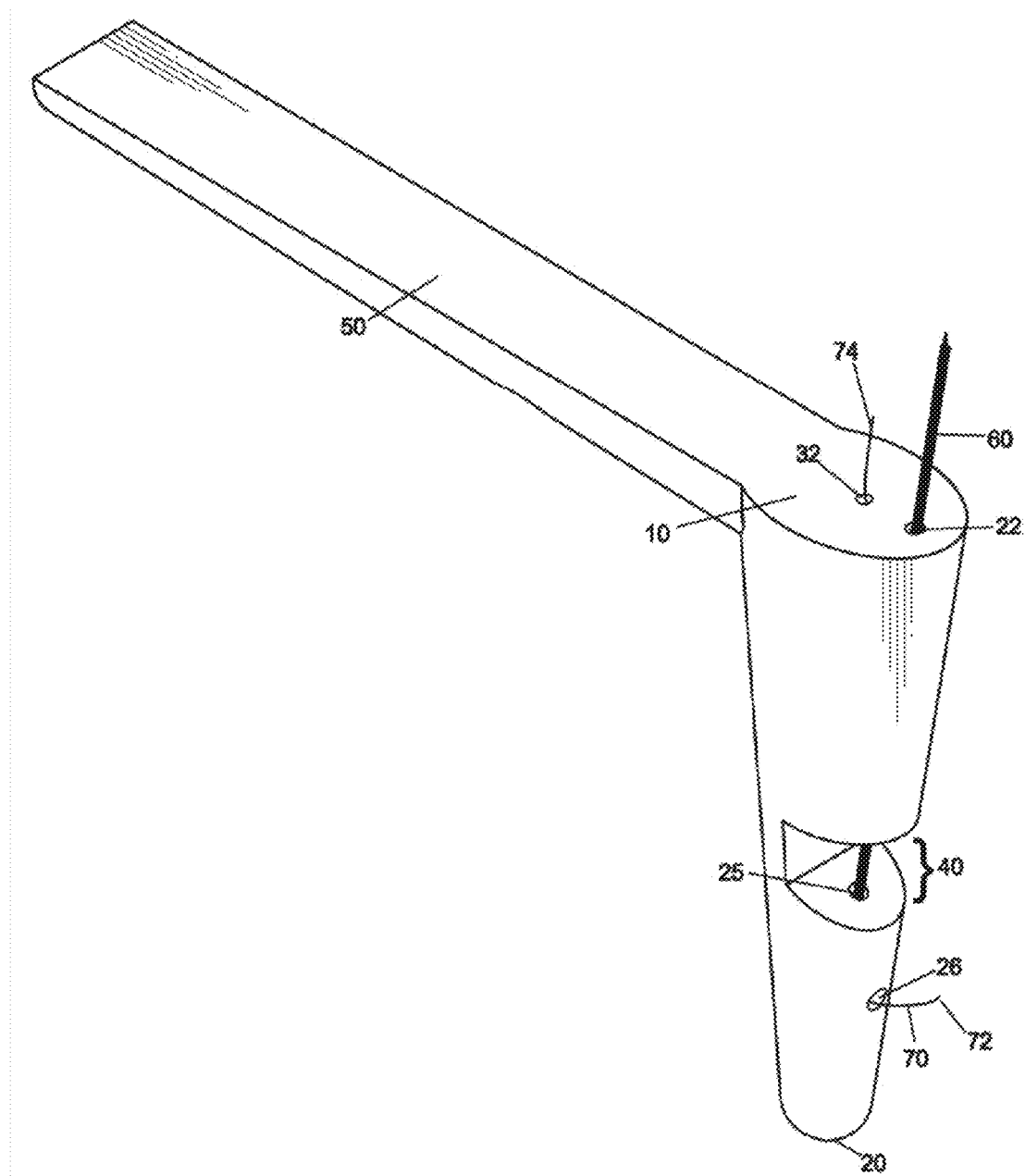
FIG. 9 shows a top and front side perspective view of a suturing device, having a needle and a suture inserted, in an embodiment of the disclosed technology.

FIG. 3 shows a cutaway side elevation view of a suturing device with a needle 60 and a suture 70 each inserted therein, in an embodiment of the disclosed technology. FIG. 9 shows a top and front side perspective view of a suturing device having a needle 60 and a suture 70 each inserted therein, in an embodiment of the disclosed technology. Now discussing FIGS. 3 and 9 simultaneously, in embodiments of the disclosed technology, the eye 62 of the needle 60 aligns with the exit portal 26 when the needle is inserted into the needle guide portal 22, past the notch 40, and at least reaching the exit portal 26. The needle 60 has an eye 62 and can or does have a length that is longer than the needle guide cavity 24.

In embodiments of the disclosed technology, the eye 62 aligns with the exit portal 26 when the needle 60 is completely inserted in the needle guide cavity 24, such that the tip of the needle is in contact with the bottom of the needle guide cavity 24. The needle 60 can be seen in the notch 40 when the needle 60 is inserted into the needle guide portal 22 and at least passes through the notch 40. Still further, the needle guide cavity 24 and/or the needle guide portal 22 can have an oval or oblong shape, forcing the needle 60 to be oriented such that the eye 62 of the needle 60 faces the exit portal 26 when the needle is inserted in the cavity.

The term "suture" is defined herein as an elongated, flexible string, thread, sinew, strand, and so on. The suture 70 has a first end 72 and a second end 74, and has a length that is longer than the length of the area between the suture guide portal 32 and the exit portal 26. Upon insertion through the suture guide portal 32, and upon being pushed through the curved suture guide cavity 34, the first end 72 of the suture 70 passes through the eye 62 of the needle 60 aligned with the exit portal 26, and exits through the exit portal 26 at substantially 90 degrees. A "double suture" can also be used with embodiments of the disclosed technology, having two strands which connect at a central area forming an "X" configuration. The method of use is otherwise the same, repeated with each of the four ends of such a suture.

Figure 4:
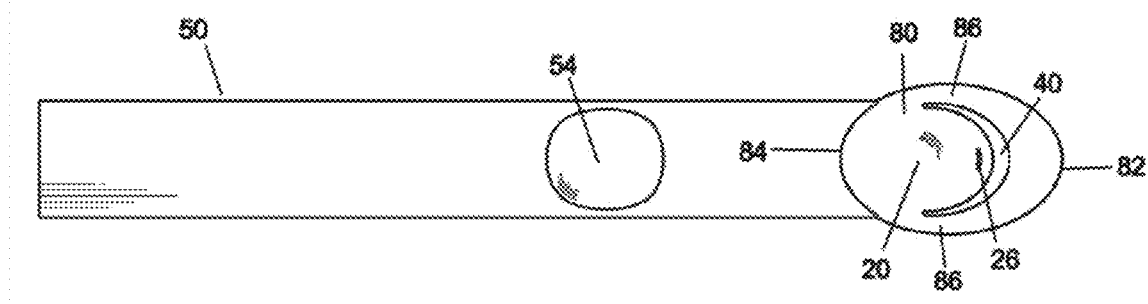
FIG. 4 shows a bottom plan view of a suturing device, in an embodiment of the disclosed technology.

FIG. 4 shows a bottom plan view of a suturing device in an embodiment of the disclosed technology. The bottom surface of the unitary handle 50 is shown with the indentation 54 for finger placement that aids in gripping the device. The elliptical cone 80 portion is shown extending from the base and narrowing until terminating at the narrowest point shown, the apex 20. The notch 40 is shown cut into the front side 82 of the cone 80 and in between the base 10 and the apex 20 of the cone 80.

Figure 5:
FIG. 5 shows a top plan view of a suturing device, in an embodiment of the disclosed technology.

FIG. 5 shows a top plan view of a suturing device, in an embodiment of the disclosed technology. In embodiments, the needle guide portal 22 and the suture guide portal 32 are situated linearly at the base 10 of the cone 80. The base is an ellipse in embodiments of the disclosed technology. The elongated handle can extend in the same line from the base 10 as the needle and suture guide portals 22 and 32 discussed above. In further embodiments, the handle need not be used. Rather, the elongated portion of the device 80 is used without a handle portion 50.

Figure 6:
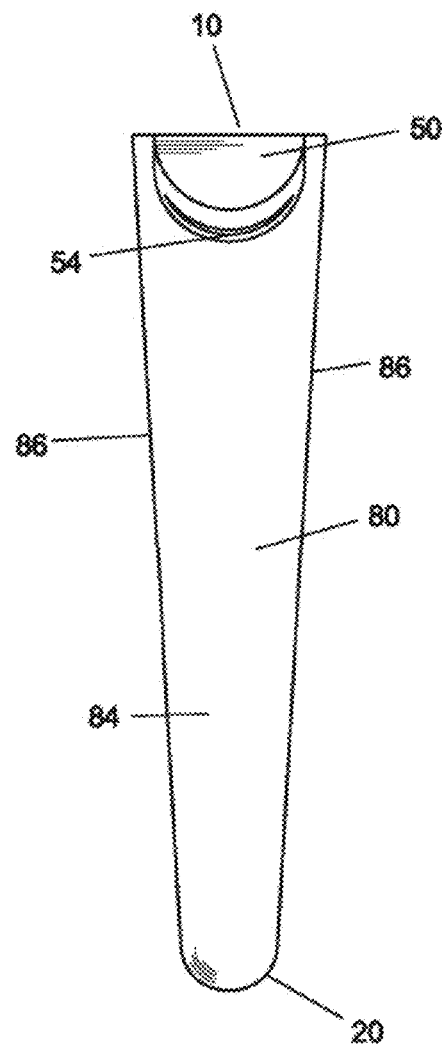
FIG. 6 shows a back side elevation view of a suturing device, in an embodiment of the disclosed technology.
Figure 10:
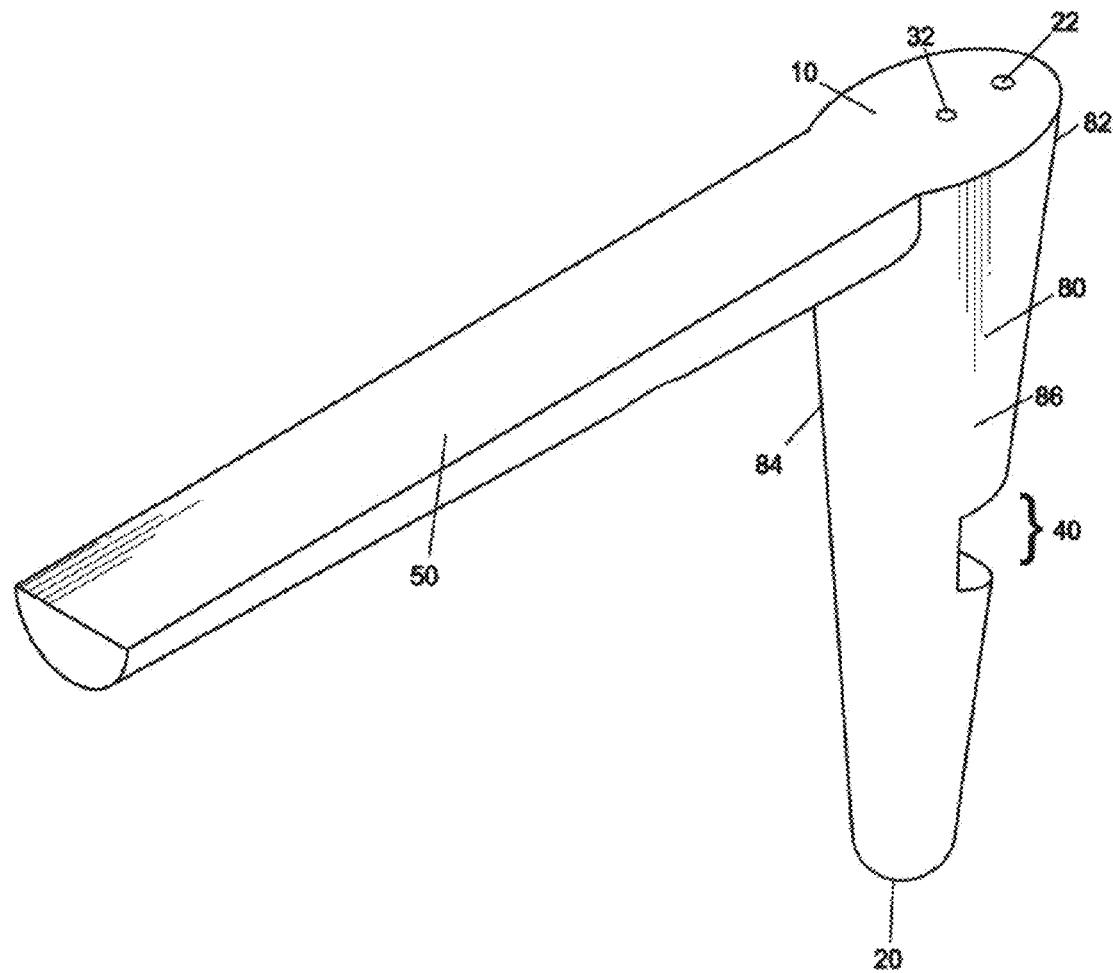
FIG. 10 shows a top and back side perspective view of a suturing device, in an embodiment of the disclosed technology.

FIG. 6 shows a back side elevation view of a suturing device in an embodiment of the disclosed technology. FIG. 10 shows a top and back side perspective view of a suturing device in an embodiment of the disclosed technology. Discussing FIGS. 6 and 10 simultaneously, the back side 84 of the elliptical cone 80 adjacent to the elongated handle 50 extends downward from the base 10, terminating at the apex 20. The handle is shown extending from the point where it meets the elliptical cone forming the acute or 90 degree angle 52, up to the tip of the handle 50. In embodiments, the finger indentation 54 is situated between the tip of the handle 50 and the angle 52 formed, where the handle 50 meets the elliptical cone 80. The notch 40 is partially cut into the side 86 of the elliptical cone between the front side 82 and the back side 84, adjacent to the elongated handle.

Figure 7:
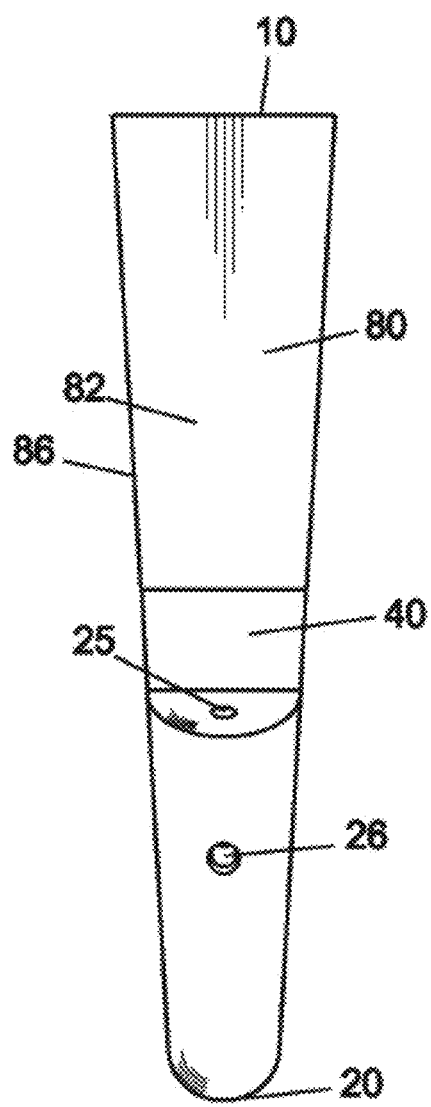
FIG. 7 shows a front side elevation view of a suturing device, in an embodiment of the disclosed technology.

FIG. 7 shows a front side elevation view of a suturing device of an embodiment of the disclosed technology. In FIG. 7, the notch 40 can be seen cut into the front side 82 of the elliptical cone portion 80, in embodiments of the disclosed technology. The second needle guide portal 25 of the needle guide cavity 24 is located on the bottom surface 46 of the device, forming the notch 40. The exit portal 26, situated perpendicularly to the needle guide cavity 24, is located at a point below the notch 40, and before the termination of the needle guide cavity 24. In another embodiment of the disclosed technology, the suture guide and needle guide cavities may be at any angle to each other and to the exterior of the suturing device as long as the cavities cross each other at some point.

Figure 11:
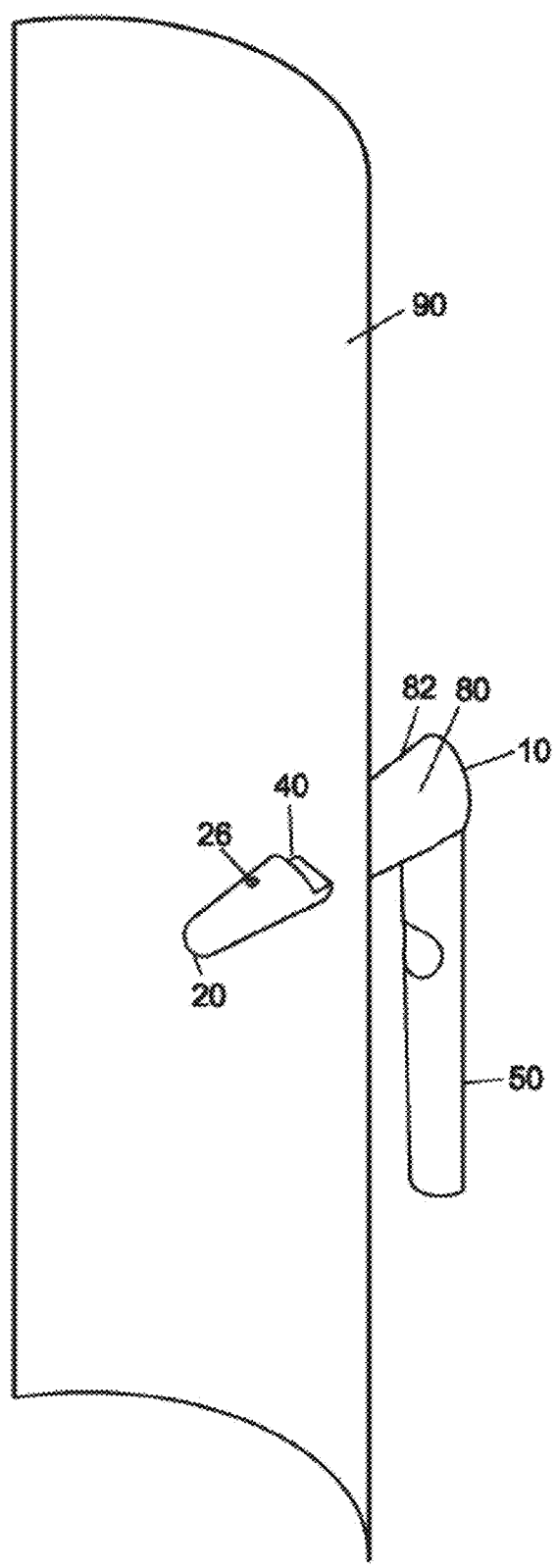
FIG. 11 shows a bottom and front side perspective view of a suturing device inserted into material, in an embodiment of the disclosed technology.
Figure 12:
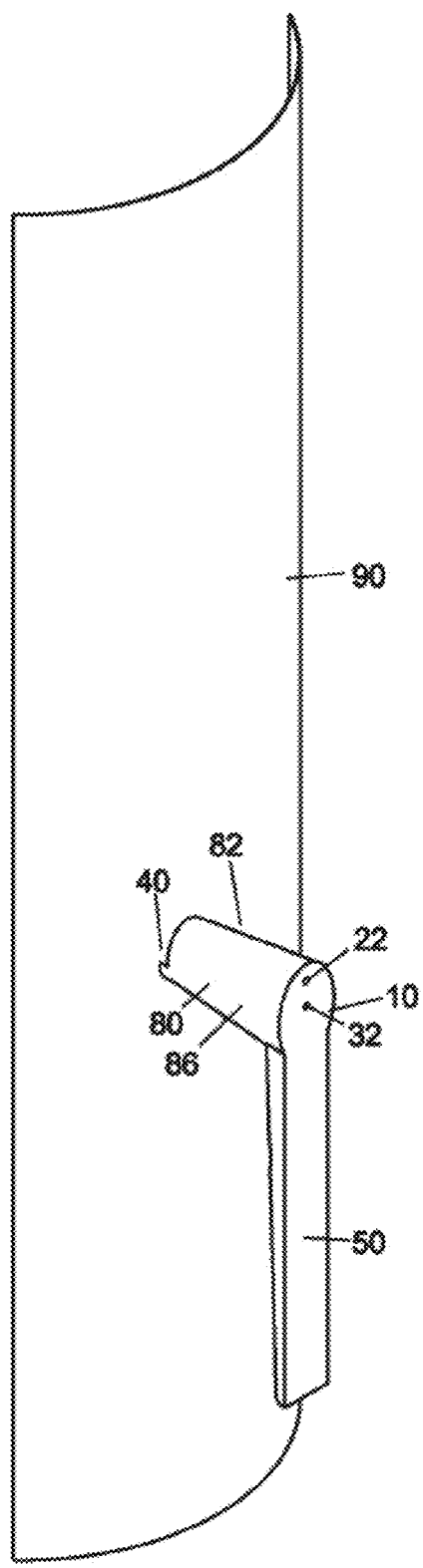
FIG. 12 shows a top and front side perspective view of a suturing device inserted into material, in an embodiment of the disclosed technology.

FIG. 11 shows a bottom and front side perspective view of a suturing device inserted into material, in an embodiment of the disclosed technology. FIG. 12 shows a top and front side perspective view of a suturing device inserted into material, in an embodiment of the disclosed technology. Now discussing FIGS. 11 and 12 simultaneously, the apex 20 of the suturing device is inserted into a preexisting hole in material 90. The device is inserted into the hole until the material 90 surrounding the hole is positioned in the notch 40. The base 10, elongated handle 50, and top portion of the elliptical cone 80 (extending between the base 10 and the notch 40) remain visible above the material. The bottom portion of the cone 80 extending between the notch 40 and the apex 20 are visible from beneath the material.

Figure 13:
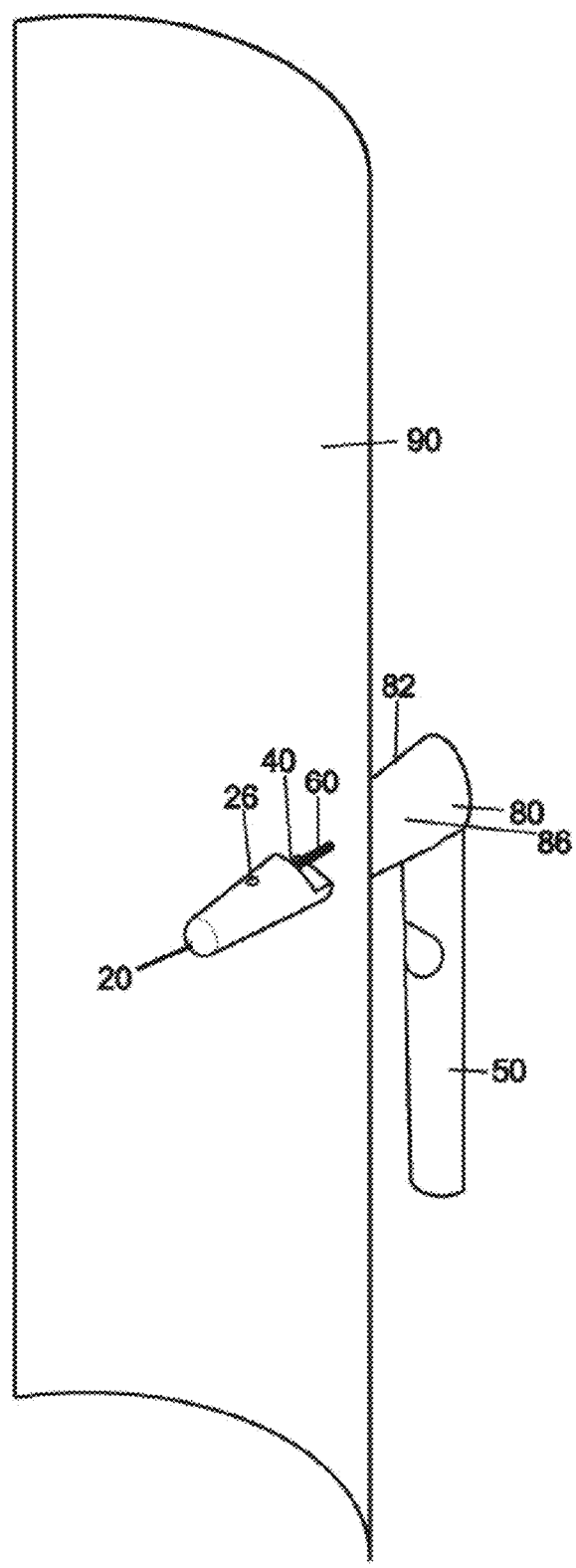
FIG. 13 shows a bottom and front side perspective view of a suturing device with a needle inserted into material, in an embodiment of the disclosed technology.

FIG. 13 shows a bottom and front side perspective view of a suturing device, with a needle inserted into material, in an embodiment of the disclosed technology. The needle 60 is inserted through the needle guide portal shown on the base 10 in FIG. 12. The needle 60 then passes through the needle guide cavity 24, penetrates through the material 90, and extends through the notch 40. The needle 60 then continues passing into the second needle guide portal 25 and into the portion of the needle guide cavity 24 below the notch 40, up to a point between the exit portal 26 and the apex 20 (both the second needle guide portal 25 and the needle guide cavity 24 not being visible in FIG. 13). The needle 60 is visible in the notch 40 beneath the material 90.

The material 90 can include any kind of medium that can be sutured. The suturing device of the disclosed technology can be used with any material 90 where one has access only to one side. Additionally, the suturing device can be used with a material 90 having a pre-existing hole, in order to sew or otherwise close the hole by sewing/attaching the material 90 around the hole. In embodiments, the material 90 can include human tissue (such as human skin or fascia), fabric, synthetics, metals (e.g., screens), and so forth.

Figure 14:
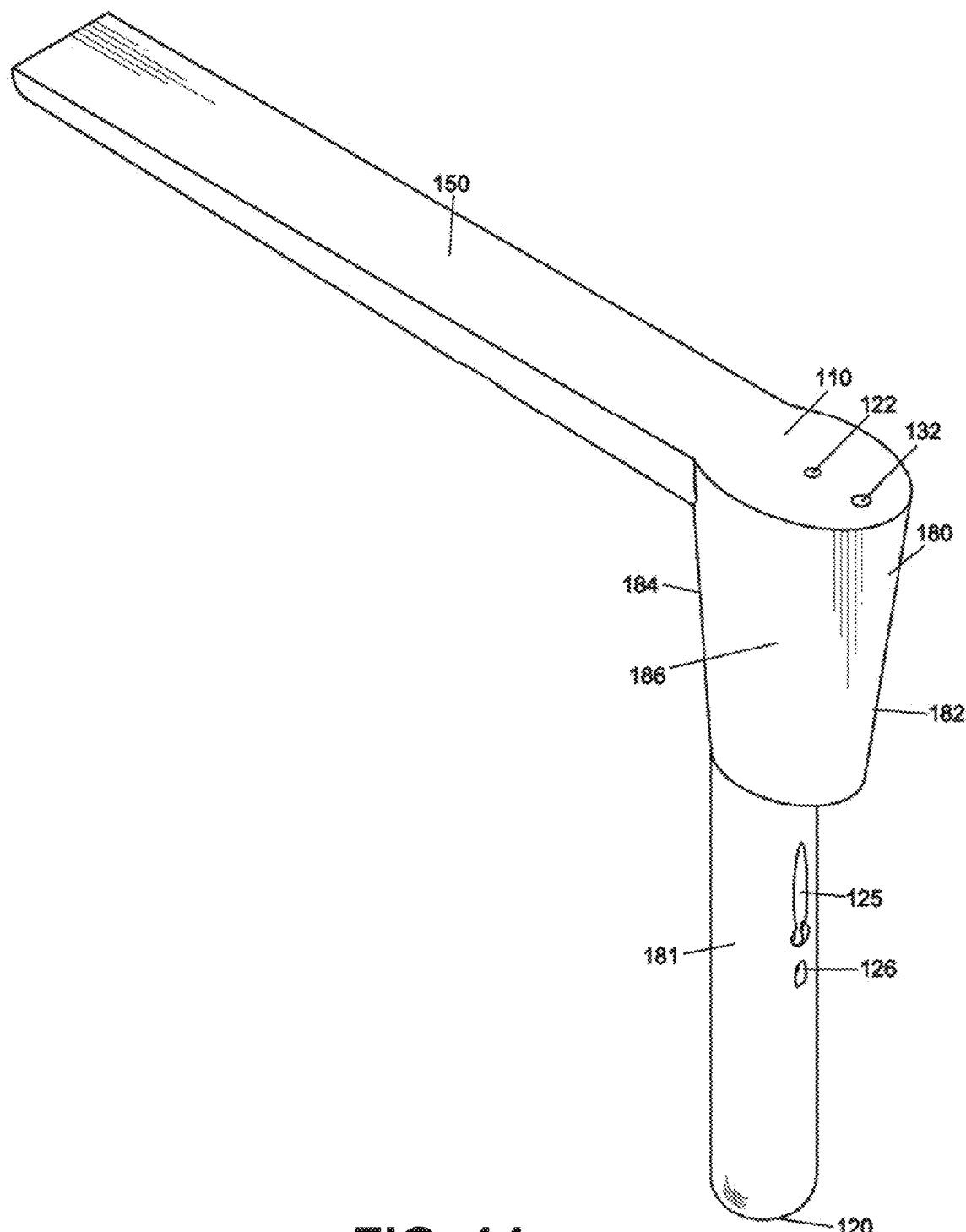
FIG. 14 shows a bottom and front side perspective view of a suturing device, in an embodiment of the disclosed technology.
Figure 15:
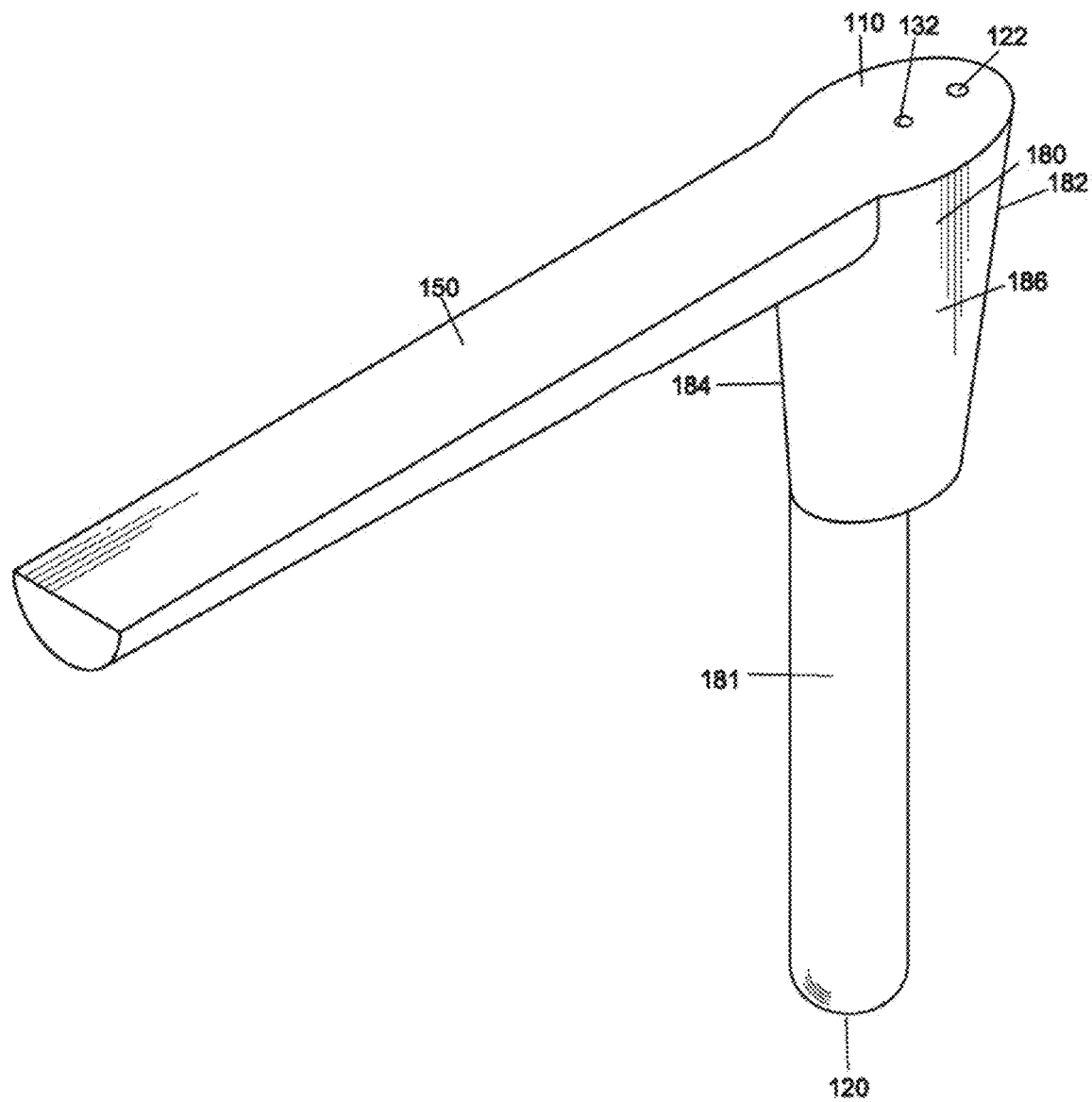
FIG. 15 shows a bottom and back side perspective view of a suturing device, in an embodiment of the disclosed technology.

FIG. 14 shows a bottom and front side perspective view of a suturing device, in an embodiment of the disclosed technology. FIG. 15 shows a bottom and back side perspective view of a suturing device in an embodiment of the disclosed technology. Discussing FIGS. 14 and 15 simultaneously, an alternative embodiment of the suturing device is shown having a uniform bottom portion 181. In this embodiment, an elongated handle 150 joins with a base 110 of a top portion of an elliptical cone 180 of the suturing device of the disclosed technology. The uniform bottom 181 joins with the cone top portion 180 on the back side 184 of the device, opposite the point where the notch 40 is located on the front side 82 of the device, in the embodiments of FIGS. 11-13. The elliptical cone top portion 180 extends between the base 110 and a bottom surface (unnumbered). The bottom portion 181 extends between a point where the bottom portion 181 joins with the top portion 180, and the apex 120.

A needle guide portal 132 is located at the base 110 of the suturing device, and a suture guide portal is located substantially at the base of the suturing device 122, in embodiments of the disclosed technology. The suture guide portal can be located at the base 110, or closer to the base 110 than the apex 120 of the suturing device. In embodiments, a first exit portal 125 and a second exit portal 126 are located on the front side 182 of the bottom portion 181 of the suturing device. The back side 184 of the elliptical cone portion 180 is adjacent to the elongated handle 150.

Figure 16:
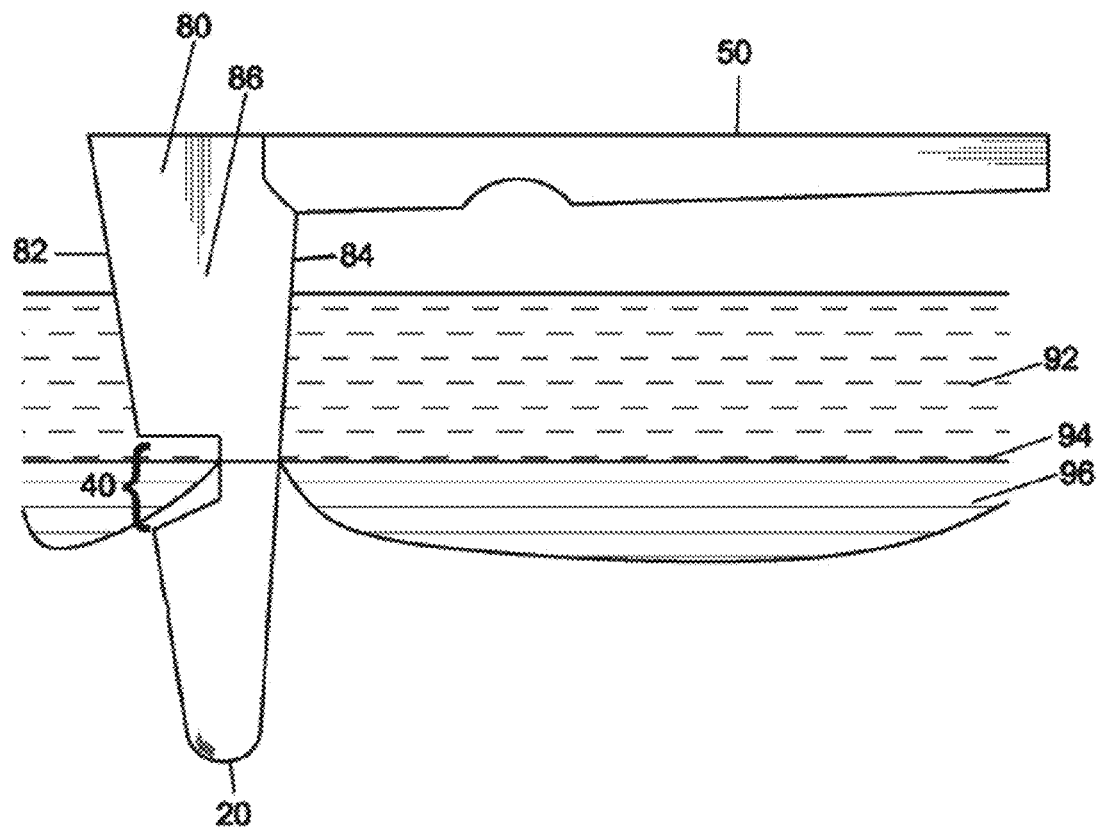
FIG. 16 shows a side elevation view of a suturing device inserted into tissue, in an embodiment of the disclosed technology.

FIG. 16 shows a side elevation view of a suturing device inserted into tissue, in an embodiment of the disclosed technology. In another embodiment of the disclosed technology, the suturing device is inserted into a preexisting hole in material 90 of FIGS. 11-13 that is mammalian or other living tissue in the current embodiment. The apex 20 of the device is inserted through the subcutaneous fat 92, fascia 94, and muscle 96 layers of tissue, so that the layers of tissue are positioned in the notch 40 of the device. The portion of the device extending below the notch 40 to the apex 20 is visible below the subcutaneous fat 92, fascia 94, and muscle 96 layers of tissue. The handle 50 and top portion extending from the base 10 to the notch 40 are visible from above the tissue. In embodiments of the disclosed technology, the suturing device can be used to close a defect in human tissue, specifically a small incision made in a minimally invasive surgical procedure, where there is access only from the outside of the tissue defect.

Figure 17:
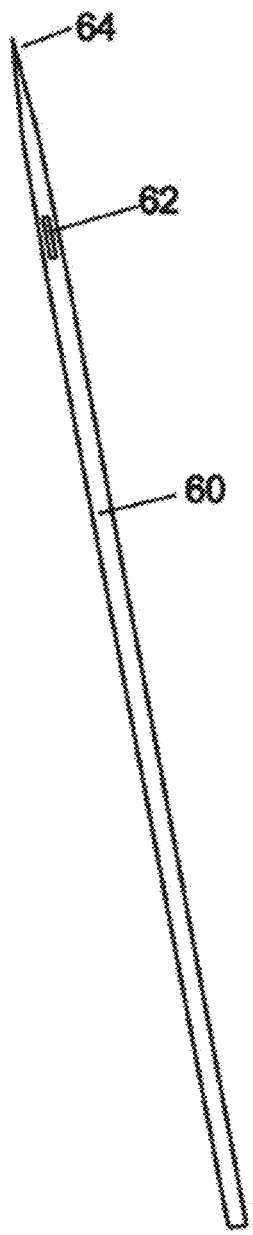
FIG. 17 shows a side view of a needle, in an embodiment of the disclosed technology.

FIG. 17 shows a needle which can be used with the suturing device of FIGS. 1-16 and 18, in an embodiment of the disclosed technology. The needle 60 has a sharp tip 64 and an eye 62. The tip 64 of needle 60 can be inserted into the needle guide portal 22 of FIG. 10 and then passed through the needle guide cavity 24 of FIG. 3. A suture 70 inserted into the suture guide cavity 34 passes through the eye 62 of the inserted needle 60 in FIG. 3, when the eye 62 is aligned with the exit portal 26. The needle 60, in embodiments, can be elliptical (having a flatter and/or more elongated front and back side and narrower left and right sides) matching that of an elliptical portal, such as that of the needle guide portal 22. This ensures that the needle 60 enters the portal in only two orientations, with the eye 62 aligning with the exit portal 26, allowing passage of a suture through the suture portal, eye of the needle, and exit portal.

Figure 18:
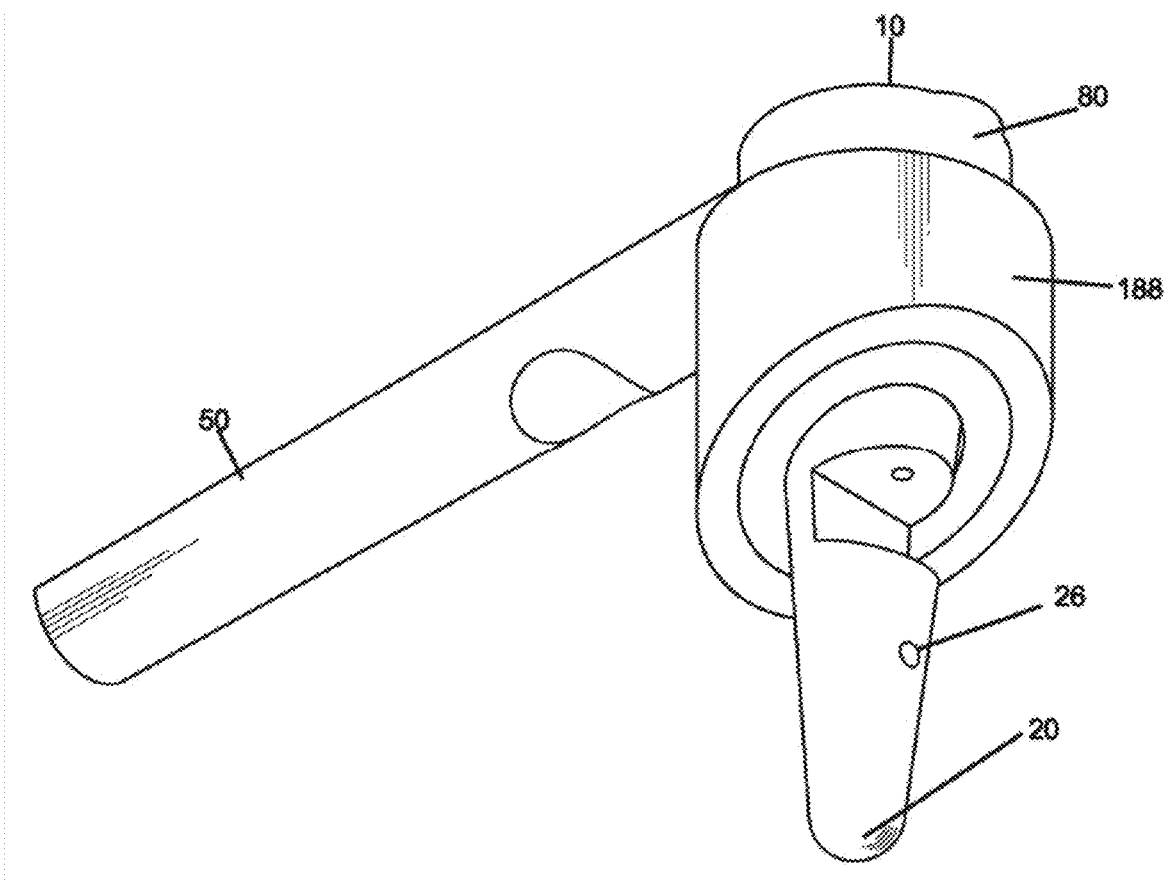
FIG. 18 shows a bottom and front side perspective view of a suturing device wrapped in insulation, in an embodiment of the disclosed technology.

FIG. 18 shows a bottom and front side perspective view of a suturing device wrapped in insulation, in an embodiment of the disclosed technology. In embodiments of the disclosed technology, at least a portion of the elliptical cone 80 above the notch 40 of the suturing device is wrapped in insulation 188 which can be foam. The insulation 188 encloses the front side 82 of the elliptical cone 80 portion of the device from a point below the base 10, substantially opposite the point where the elongated handle 50 joins with the elliptical cone 80.

The insulation 188 additionally encloses the two sides 86 adjacent to the front side 82 from a point below the base 10, substantially adjacent to where the handle 50 meets the elliptical cone 80, to a point above the notch 40, and above the exit portal 26, in embodiments of the disclosed technology. The back side 84 is enclosed in insulation 188 from a point substantially where the handle 50 meets the elliptical cone 80 below the base 10 of the suturing device, to a point substantially at the apex 20. In embodiments, the elongated handle 50, the base 10, the exit portal 26, the notch 40 and the apex 20 remain visible.

Figure 19:
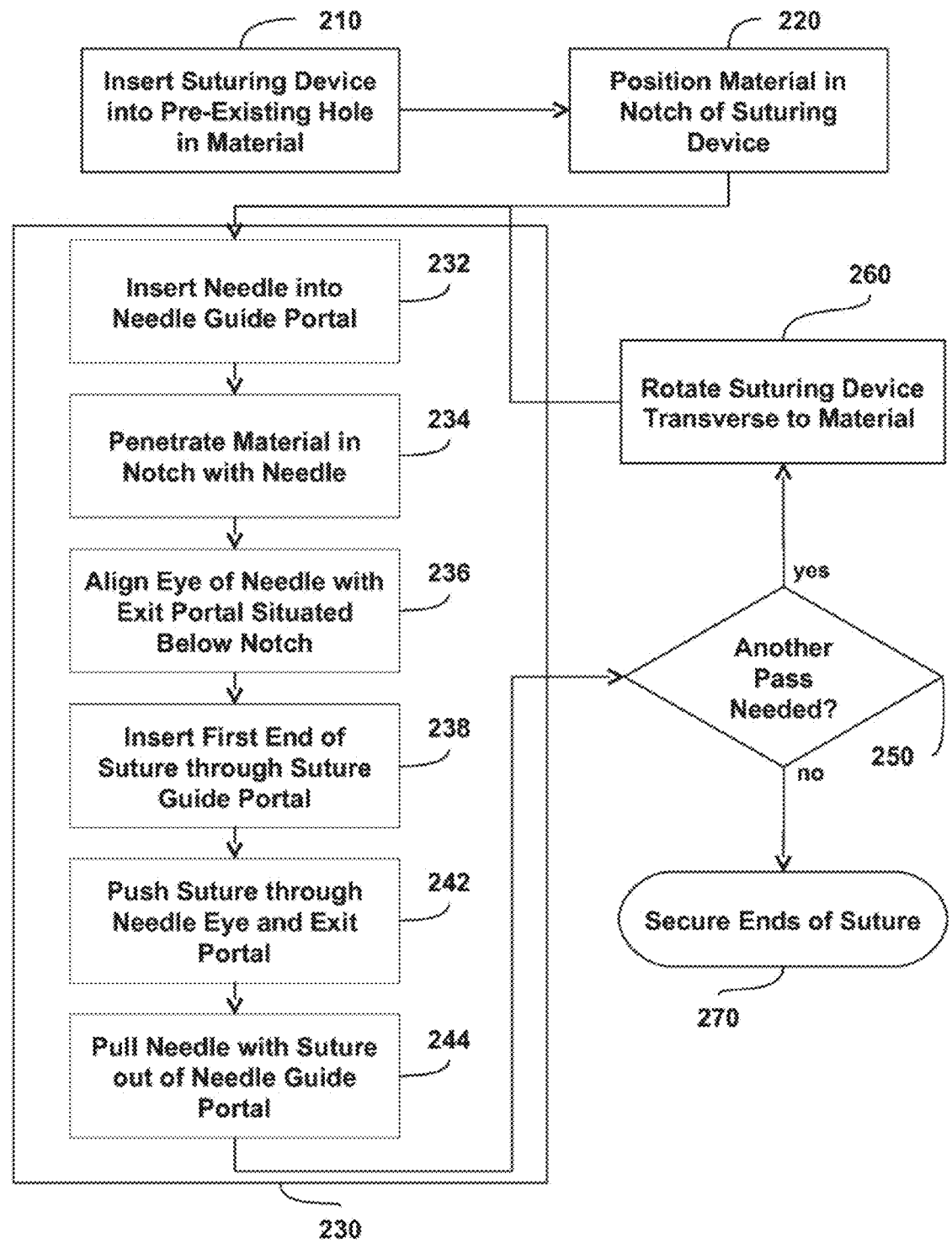
FIG. 19 shows a high level flow chart of a method of suturing a hole with a suturing device, in an embodiment of the disclosed technology.

FIG. 19 shows a high level flow chart of a method of suturing a hole with a suturing device, in an embodiment of the disclosed technology. In a first step 210, the suturing device is inserted into a pre-existing hole in material. The material is then positioned within a notch of the device in step 220. In embodiments without a notch, the material is simply positioned below a needle cavity, so that a needle can be inserted into the material. This is further described in steps 232 and 234, respectively, where a needle is inserted into a needle guide portal and then penetrated into the material. Where a notch (cutout into the body of the suturing device) is present, the material is positioned in the notch and the needle passes through the material, also in the notch.

Then, in step 236, the eye of a needle is aligned with an exit portal of a suture. A suture, or other elongated thread used to sew, is inserted into another portal, such as that located at the top (base) of the suturing device, and extends through a cavity where exiting, at an exit portal, at a location of, or at a height of, an eye of the needle after the needle has passed through the material. This may be accomplished further by way of step 238, inserting the suture into a suture guide portal (step 242), and pushing the suture through the needle eye and an exit portal. Then, in step 244, the needle is pulled out of the suturing device with the suture still passing through the eye of the needle. The needle and suture pass through the material, such that a first half of a stitch is made with the suture extending from the back side of the material (opposite side from a direction of entry of the suturing device). This completes a first pass of the sewing steps of box 230.

After the first pass, another pass will be needed to complete the stitch. As such, in step 250, the decision "yes" is made to another pass being needed. Step 260 is then carried out, and the suturing device is rotated transverse (or orthogonal) to the material. Then, a second end of the suture is inserted and the sewing steps in box 230 are repeated. After completing this second pass, the suture now passes through the material at two spaced-apart locations, with the ends of the suture both extending towards the direction in which the suturing device was inserted (such as outward from the body of a patient being sewn).

More passes can be used, or, alternatively, after decision box 250, step 270 is carried out, and the ends of the suture are secured together, such as by tying. It should further be noted that a portal of the suturing device used for entry of the needle in this method may be elongated, so that a similarly shaped needle can enter only in a direction such that the eye of the needle is perpendicular to the direction of a suture.

Referring again to FIG. 19, the method of use will now be described with reference to the device shown in FIGS. 1-10, as well as such a device shown inserted into material, shown in FIGS. 11-12. In step 210 of embodiments of the method, the suturing device is inserted into a pre-existing hole in a material such as material 90, shown in FIGS. 11-13, or tissue, shown in FIG. 16. This may be accomplished by first inserting an apex 20 of the suturing device into a hole. Following the insertion, in step 220, the material 90 is positioned within a notch 40 of the suturing device. The notch, as described above, such as with reference to FIG. 1, is cut into one side of the suturing device between the base 10 and the apex 20 thereof.

In the series of suturing steps 230, the hole is sutured with the device and a needle 60. In the first step of suturing, that is, in step 232, the needle 60 is inserted into a needle guide portal 22 and into the needle guide cavity 24. (The needle may be partially inserted into the needle guide portal before steps 210 and 220). In step 234, after insertion of the needle 60 into the needle guide portal 22, the needle penetrates the material 90 in the notch. This can be seen in FIGS. 11 and 13, FIG. 11 showing the device inserted into the material before the needle, and FIG. 13 showing the needle passing through the material. The needle is inserted into the needle guide portal and can penetrate the material at an angle orthogonal to a plane passing substantially through the hole and the material. In step 236, the needle then passes through the needle guide cavity 24 below the notch, and an eye of the needle 62 is aligned with an exit portal situated between the notch and the apex of the device, such as exit portal 26 shown in FIG. 13.

Still describing the current method, in step 238, a first end of a suture 72 is inserted through a suture guide portal located substantially at the base 20 of the suturing device. The suture then passes through a suture guide cavity, such as suture guide cavity 34, and is pushed through the eye of the needle 62, as well as through the exit portal 26 in step 242, exiting via the exit portal. The angle of the exit of an end 72 (or 74, in a second pass) of the suture 70 can be 90 degrees from the angle of entry of the suture through the suture entry portal 32. In step 244, the needle 60 is then at least partially extracted with the suture from the needle guide portal 22 of the suturing device. In this step, the suture 70, still passing through the eye of the needle, passes back through the material at a point of the needle penetration, pulling the suture there-through.

Following the completion of the series of steps 230, a determination is made as to whether another pass of the needle and suture is needed in step 250. If it is determined that another pass of the needle and suture are needed through the material, in step 260, the suturing device is rotated transverse to the material with respect to the hole (e.g., approximately 180 degrees), such that another insertion of the needle now can proceed at a second point of penetration of the material. Then, the series of steps 230 are repeated at a second position of the material, and with a second end of the same suture used, or with an additional suture. If it is determined in step 250 that an additional pass in not needed, the suture device may then be extracted from the hole. Once the suture has passed through the second point of penetration, the suture extends both into and out of the material at different points around the hole and can be secured in step 270 of the method.

Now discussing FIG. 19 in view of FIGS. 11-13 and 16, in embodiments, the pre-existing hole can be a tissue defect, and the material around the hole can constitute bodily tissue. In further embodiments, the method can additionally include a step of removing a trocar from a tissue defect before the step 210 of inserting the suturing device. The step 210 of inserting a suturing device into a pre-existing hole can further include rotating and manipulating the device, while maximizing an amount of tissue positioned in the notch, in embodiments of the disclosed technology. The step 244 of pulling a needle with suture out of needle guide portal can further include completely extracting the needle from the suturing device.

In embodiments, the step 260 of rotating the suturing device can further include rotating the device substantially 180 degrees. Additionally, the suturing device can be elliptical, such that rotating the device substantially 180 degrees causes the tissue defect to stretch, such that first and second points of penetrating are spaced further apart, as compared to carrying out the method with a corresponding circular device, in embodiments of the disclosed technology. The step 270 of securing the ends of the suture can first include a step of extracting the suturing device from the hole. In embodiments, the first suture can be looped through a second suture, such that each end of the first and second sutures can be inserted through the suture guide portal after each step 232 of inserting the needle and each step 234 of penetrating the material.

Figure 20:
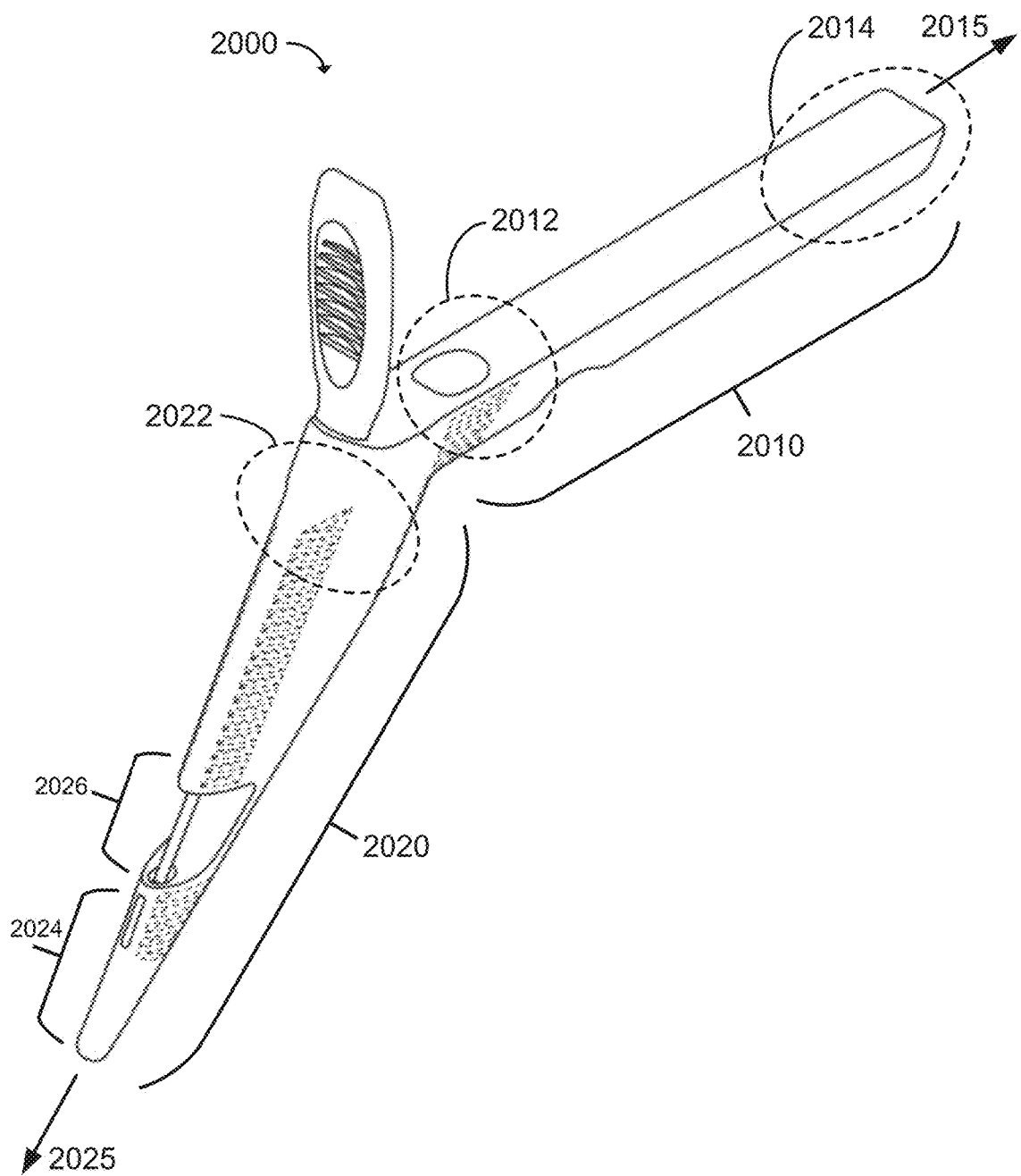
FIG. 20 shows a top and front side perspective view of the suturing device, in an embodiment of the disclosed technology.

FIG. 20 shows an illustrative suturing device 2000 (e.g., a fascial closure device), according to various embodiments. Embodiments of the suturing device 2000 can be implementations of devices described above, and/or can operate according to methods described above. As illustrated, embodiments include a handle structure 2010 and a guide structure 2020. The handle structure 2010 can extend primarily along a first vector 2015 between a first coupling region 2012 and a handle region 2014. The guide structure 2020 can extend primarily along a second vector 2025 between a second coupling region 2022 and a distraction region 2024. The second coupling region 2022 can be coupled with the first coupling region 2012 in any suitable manner. In some implementations, the handle structure 2010 and the guide structure 2020 are separable (e.g., provided as a kit) and can be assembled using fasteners, snapped together, and/or otherwise coupled together at the second coupling region 2022 and the first coupling region 2012. In other implementations, the handle structure 2010 and the guide structure 2020 are formed as a unitary structure (e.g., manufactured as one piece or assembled as part of the manufacturing process), so that the second coupling region 2022 and the first coupling region 2012 are manufactured as coupled together (i.e., the term "coupled" can describe active coupling of separable pieces or simply the physical arrangement of two portions of a single unitary piece). The guide structure 2020 can further include a material capture region 2026 located between the second coupling region 2022 and the distraction region 2024.

Figure 21:
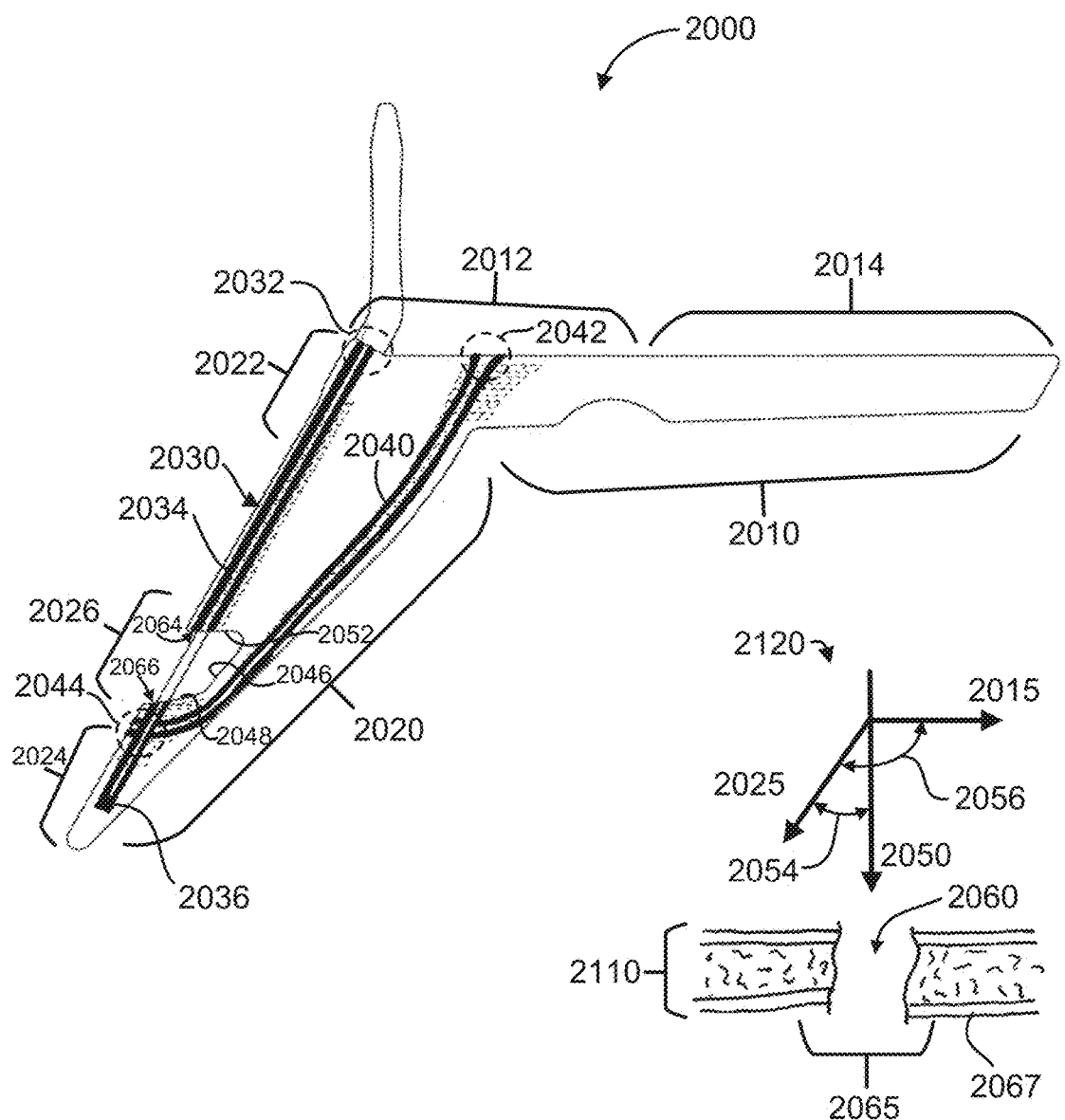
FIG. 21 shows a side view of the suturing device and a side view of a tissue defect, in an embodiment of the disclosed technology.

FIG. 21 shows a side view of a suturing device 2000 in an embodiment of the disclosed technology. The suturing device 2000 can be an implementation of the suturing device 2000 of FIG. 20. For context, FIG. 21 also shows a side view of a tissue defect region 2110 and a guide 2120 indicating various reference directions and angles. As illustrated, the suturing device 2000 can further include a needle guide cavity 2030 and a suture guide cavity 2040. The needle guide cavity 2030 can extend along a needle path that originates at a needle guide portal 2032 in the handle structure 2010 and passes only partially through the guide structure 2020, interrupted by the capture region 2026. The suture guide cavity 2040 can extend along a suture path that originates at a suture guide input portal 2042 in the handle structure 2010 and terminates at a suture guide exit portal 2044 in the guide structure 2020.

In embodiments shown in FIGS. 1-18, the handle and guide structures are oriented to form an acute or approximately 90-degree angle (i.e., an 'L' shape), although other configurations are possible. As illustrated in FIG. 20, some embodiments of the handle structure 2010 and the guide structure 2020 can be coupled to form an obtuse angle. For example, the second coupling region 2022 can be coupled with the first coupling region 2010 to form an obtuse angle 2056 between the first vector 2015 and the second vector 2025. Trials of the device have demonstrated that an obtuse angle can facilitate distraction of multiple tissue layers around a defect with less pushing exertion by the user. For example, as illustrated in FIG. 21, a defect, such as hole 2060 in tissue resulting from removal of a laparoscopic trocar, in material 2065 can define a hole axis 2050 that passes through the hole 2060, and the hole axis 2050 can be substantially normal to an inner surface 2067 of the material 2065 adjacent to the hole. As used herein, the term hole 2060 is being used interchangeably with the term defect. Thus, the term hole is being used broadly to encompass anything that may be considered a defect. For example, after removal of a trocar during a laparoscopic procedure the defect that was previously held open by the trocar may partially or completely close to form a straight line defect between opposing edges of the previously opened wound. In this example, the term hole is intended to encompass any opening, interruption, and/or the like, such as the straight line defect left by an incision and/or removal of a trocar. When the handle structure 2010 of the suturing device 2000 is held substantially parallel with the outer surface of the material 2065 surrounding the hole 2060, the guide structure 2020 is oriented off-axis from the hole axis 2050. For example, the second vector 2025 and the hole axis 2050 form an acute angle 2054 (e.g., between 20 and 70 degrees).

The disclosure makes reference to various relationships (e.g., angles, directions, orientations, etc.) between the suturing device 2000, human anatomy and structures associated with tissue defects, such as the acute angle 2054 between the second vector 2025 to the hole axis 2050 that can occur during use of the suturing device 2000. The relationships disclosed herein are intended to be illustrative and provide relative guidance as to how various aspects of these components interact. However, it will be appreciated that the present disclosure relates to surgical procedures performed on living organisms, and therefore, variations in these relationships are inherent. Thus, the description is presented for purposes of illustration and is not intended to limit the invention to the forms disclosed herein. Consequently, variations and modifications commensurate with the following teachings skill and knowledge of the relevant art, are within the scope of the present disclosure.

As further illustrated in FIG. 21, the material capture region 2026 comprises a notch cut-out 2046 that defines an inner capture feature 2048 oriented according to the first vector 2015. In this embodiment, the inner capture feature 2048 is substantially parallel to the handle structure 2010. In this regard, when the guide structure 2020 is inserted in the hole 2060 with the handle structure 2010 located outside the hole 2060 and oriented so that the first vector 2015 is substantially perpendicular 2056 to the hole axis 2050, the inner capture feature 2048 is located below the inner surface 2067 of the hole 2060 and is substantially coplanar with the inner surface 2067 of the material 2065 adjacent to the hole 2060. The notch cut-out 2046 defines an outer capture feature 2052 positioned to be located above the material 2065 adjacent the hole 2060 when the inner capture feature 2048 is located below the material 2065 adjacent the hole 2060. The needle path defined by the needle guide cavity 2030 comprises a first sub-path 2034 that originates at the needle guide portal 2032 and ends at an opening 2064 in the outer capture feature 2052, and a second sub-path 2036 that originates at an opening 2066 in the inner capture feature 2048 and ends within the distraction region 2024. The first sub-path 2034 is aligned with the second sub-path 2036, such that the needle guide cavity 2030 is interrupted by the capture region 2026.

Figure 22:
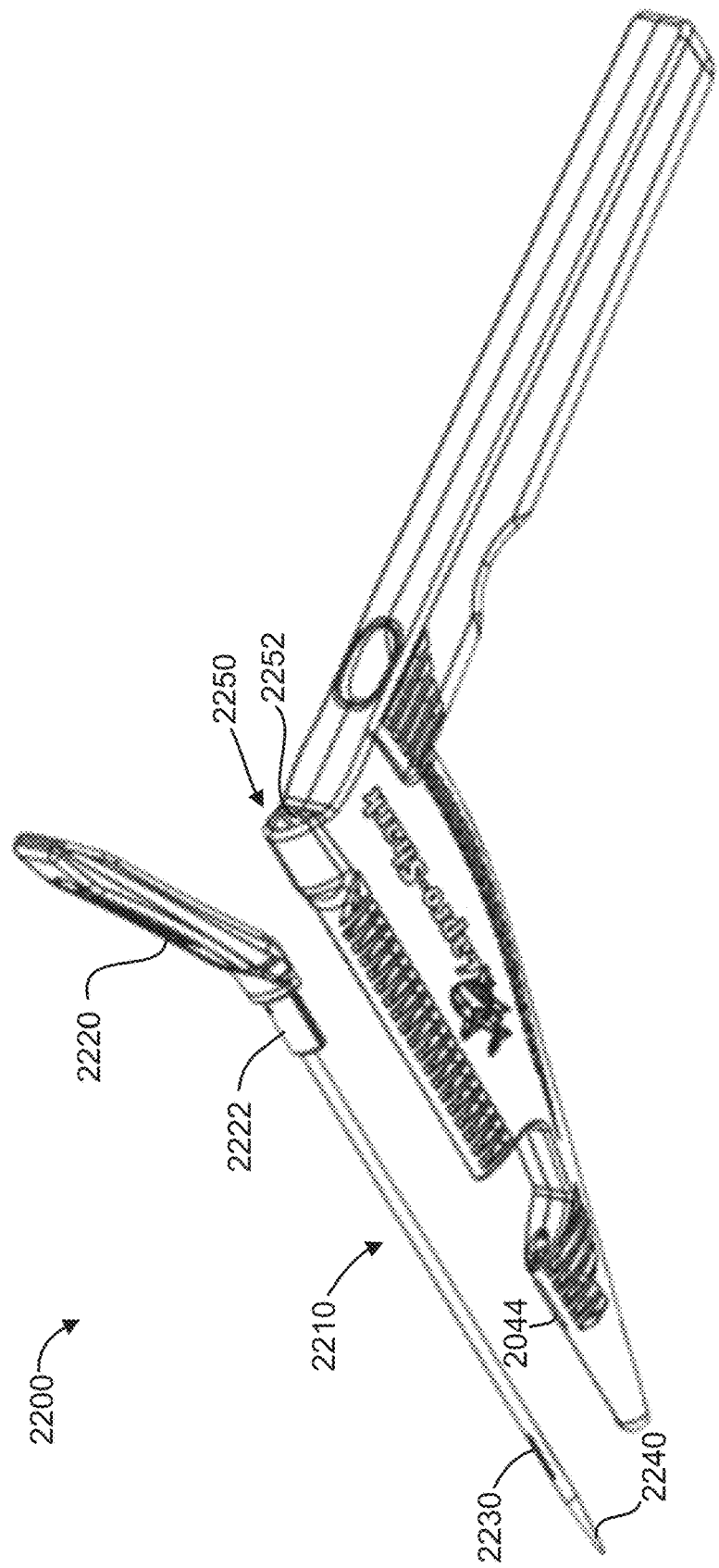
FIG. 22 shows a top and front side perspective view of the suturing device and needle, in an embodiment of the disclosed technology.

FIG. 22 shows a top and front side perspective view of a suturing device 2200, in an embodiment of the disclosed technology. The suturing device 2200 can be an implementation of the suturing device 2000 of FIGS. 20 and 21, and aspects of the suturing device 2200 are described in context of features of the suturing device 2000 (some of which are not detailed in FIG. 22 to avoid over-complicating the illustration). As illustrated, the suturing device 2200 has a needle 2210 shaped according to the needle path. For example, if the needle path, defined by the needle cavity 2030, has a circular cross-sectional profile then the needle 2210 can also have a circular cross-section profile. In this embodiment the needle 2210 has a needle handle 2220, a needle eye 2230, and a needle tip 2240. The needle 2210 is sized, so that, when the needle is inserted into the needle guide cavity 2030, the needle handle is proximate to the needle guide portal 2250. Therefore, when the needle eye 2230 is within the material capture region 2026 and the needle tip 2240 is within the distraction region 2024, the handle 2220 of the needle 2210 protrudes from the needle guide portal. The needle guide portal 2250 also has a needle orientation feature 2252 that interfaces with the needle 2210 to rotationally align the needle eye 2230 with the suture guide exit portal 2044. The needle orientation feature 2252 can have an asymmetric structural feature (e.g., a D-shaped profile, patterned feature such as a star profile, notch and/or the like) that interfaces with a corresponding needle alignment feature 2222 on the needle 2210. In this regard, the needle alignment feature 2222 can only engage with the needle orientation feature 2252 located on the handle 2000 in a single orientation. This single orientation corresponds to the needle eye 2230 aligning with the suture exit portal 2044. In one embodiment, the suturing device 2000 and the needle 2210 are provided in a kit. These components may be packaged together or separate and can come in surgical packaging (e.g., sterilized and/or sterilizable blister packaging, molded disposable packaging, and/or the like).

Other such features relate to novel aspects of the suturing device. As illustrated, the needle path can be linear such that the needle cavity extends in a straight line between the needle guide portal 2032 and the second sub-path 2036. In one embodiment, the handle 2220 and needle alignment feature 2222 are manufactured as a unitary structure. The needle handle 2220 can be angled forward (e.g., away from the handle structure 2010, as illustrated) to provide a surgeon more space for manipulating the suture into the suture guide input portal 2042.

Figure 23:
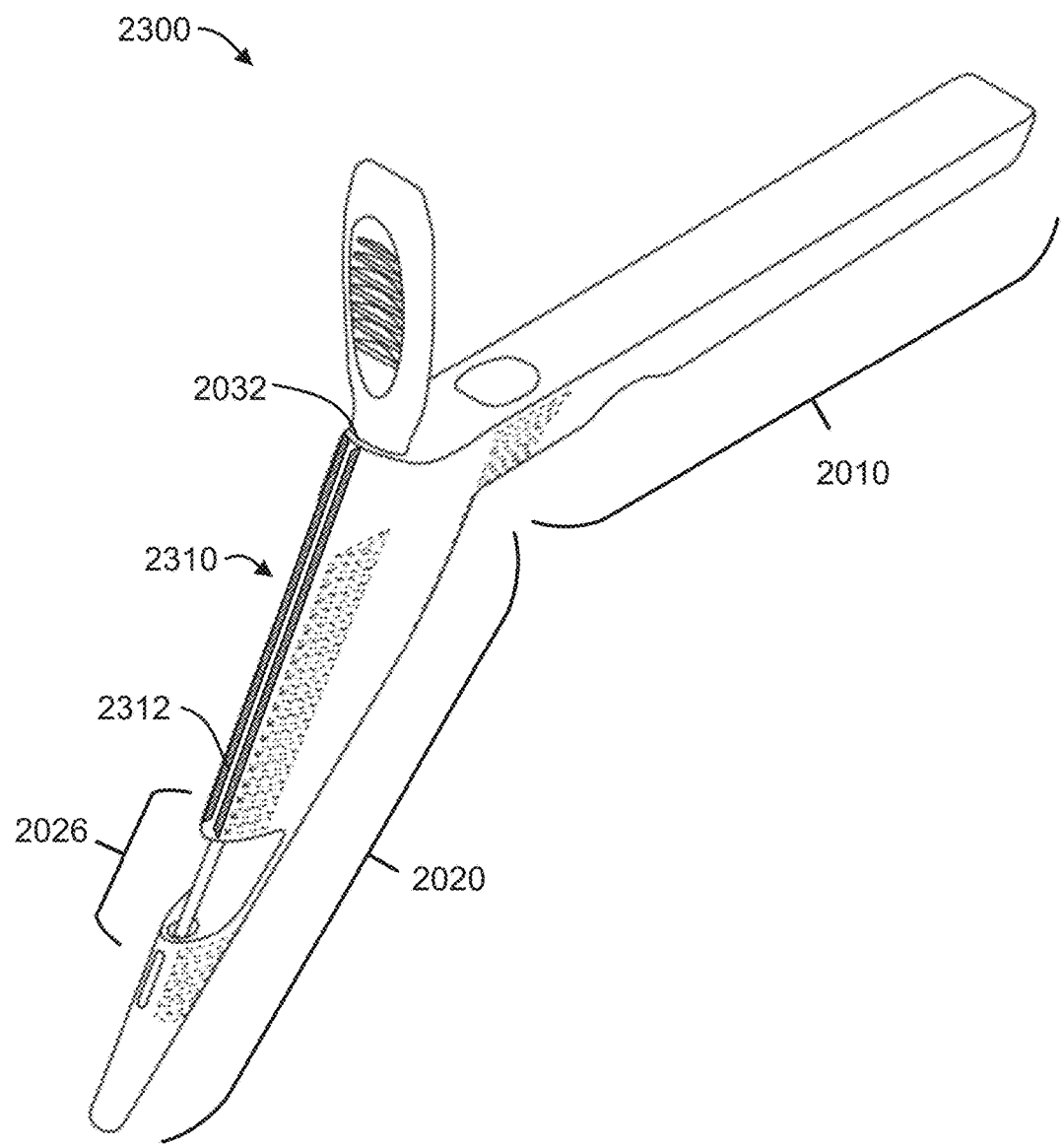
FIG. 23 shows a top and front side perspective view of the suturing device with a release substructure, in an embodiment of the disclosed technology.

FIG. 23 shows a top and front side perspective view of a suturing device 2300, in an embodiment of the disclosed technology. The suturing device 2300 can be an implementation of the suturing device 2000 shown in FIGS. 20-21 and/or 2200 shown in FIG. 22. Aspects of the suturing device 2300 are described in context of features of the suturing device 2000 (some of which are not detailed in FIG. 23 to avoid over-complicating the illustration). The suturing device 2300 has a release substructure 2310 formed in the handle structure 2010 and guide structure 2020. The release substructure extends along the needle guide cavity 2030 (e.g., described with reference to FIG. 21) between the needle guide portal 2032 and the material capture region 2026. The release substructure 2310 has a suture passage 2312 sized to permit a suture to pass through. For example, opposing walls of the suture passage 2312 are in contact, and upon tensioning a suture located within the needle guide cavity 2030 the suture can slide between the opposing sides of the suture passage 2312 to be released from the suturing device 2000. After release of a suture from the suturing device 2000, the suture is free from the suturing device and can be to be tied off to close a defect in the hole 2060 without removing the suturing device 2300 from the hole 2060. Such a feature permits the suturing device 2300, while still positioned within the hole 2060, to be manipulated into a new orientation. For example, without removing the suturing device 2300 from the defect 2060, the suturing device 2300 can be used to place (and tie) multiple sutures by rotating the suturing device 2300 substantially around the hole axis 2050 (e.g., shown in FIG. 21) between each suturing procedure.

Figure 24:
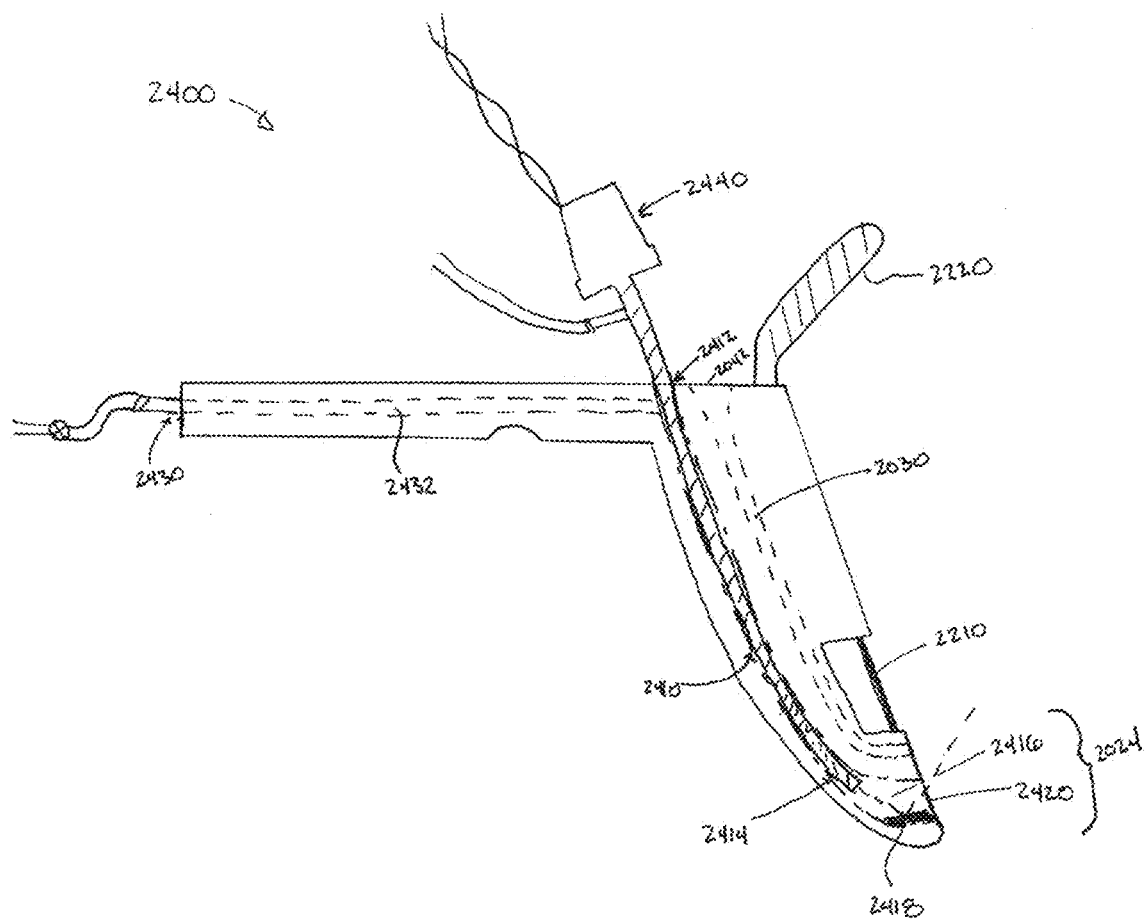
FIG. 24 shows a side view of the suturing device with an instrument cavity, in an embodiment of the disclosed technology.

FIG. 24 shows a side view of a suturing device 2400, in an embodiment of the disclosed technology. The suturing device 2400 can be an implementation of other embodiments of suturing devices described herein. Aspects of the suturing device 2400 are described in context of features of the suturing device 2000 (some of which are not detailed in FIG. 23 to avoid over-complicating the illustration). The suturing device 2400 has an instrument guide passage 2410. The instrument guide passage 2410 extends from an instrument guide portal 2412 to an instrument exit portal 2414 located in the distraction region 2024. The instrument guide passage 2410 is sized to receive a laparoscopic instrument such as a laparoscopic camera 2440. The instrument exit portal 2414 also has an instrument cavity 2416 located within the distraction region 2024. In this regard, the instrument cavity can be used to aid a laparoscopic instrument. For example, the instrument cavity 2416 can have a mirror 2418 oriented opposite from the viewing end of laparoscopic camera in the distraction region 2024. The mirror 2418 is oriented such that the laparoscopic camera 2440 can view a suture exiting the suture exit portal 2044 by way of the mirror 2418. The instrument cavity 2416 can include a window 2420 that allows the laparoscopic camera 2430 to view the area around the distraction region and/or material capture region. The window 2420 can be substantially flush with the surface of the distraction region 2024 to help facilitate insertion and removal of the distraction tool from a hole 2060. For example, the window can be shaped to, coupled with, integrated with, and/or otherwise implemented, so that the surface of the distraction region is sufficiently smooth (and/or otherwise free of protrusions or other features) to avoid catching on material 2065 located adjacent to the hole 2060. In various embodiments, other means can be used to view the area below the inner surface 2067. In certain embodiments, reflective, refractive or other methods of bending light can be used to allow visualization of the penetration location, the suture guide exit portal 2044, the suture 2620, and/or any combination of these components, as well as other structures or features located around the penetration location of material 2065 adjacent the hole 2060. For example, a prism could be located in the instrument guide cavity 2416 to refract the images from the penetration location. In alternative embodiments, the instrument cavity 2416 could be enclosed by an access door, which provides a barrier surface between the instrument cavity 2416 and the surrounding environment. In such an embodiment, the access door can open to permit passage of another laparoscopic instrument into the region below the inner surface. The laparoscopic instrument can be a camera used to view the region of material 2065 adjacent the hole 2060, the guide structure 2020, the suture guide exit portal 2044, and/or other components of the suturing device 2000, or features in this region. In other embodiments, the instrument cavity 2416 or access door can include features that help orient the laparoscopic instrument.

FIG. 24 also illustrates an embodiment of the suturing device having an insufflation port 2430. The insufflation port originates on the handle region 2014, and extends along an insufflation cavity 2432 to an insufflation exit port 2434 located on the guide structure 2020. The insufflation cavity 2432 provides a conduit between a gas source (e.g., pressured carbon dioxide) and a cavity that the guide structure 2020 is at least partially inserted into (e.g., an abdominal cavity). Pressurized gas can then be injected into the cavity through the suturing device 2400 to inflate an abdominal cavity. In alternative embodiments, the insufflation cavity 2432 could be combined with other ports such as the instrument guide portal 2412. For example, the insufflation cavity 2432 could extend between the insufflation port 2430 and the instrument guide cavity 2410, where the gas would then travel at least partially through the instrument cavity 2410 to an exit on the guide structure 2020. In this embodiment the instrument guide portal could have a valve or adapter structure to prevent gas from escaping at this location.

In other embodiments, the suturing device 2400 can have multiple instrument guide cavities 2410 extending between a location on the handle 2010 and a location on the guide structure 2020. Additionally, various guide passages could join to share a single cavity and/or have different ports configure to receive specific instruments. For example, the insufflation port 2430 could be configured to accept a luer type connector from a gas source and the instrument guide portal 2412 could be configured with a Tuohy Borst or similar adapter to prevent backflow of gas or other fluids around a laparoscopic instrument inserted into the instrument guide portal 2412. Various implementations of the suturing device 2400 can include only the one or more instrument guide portal(s) 2412, only the insufflation port 2430, both the instrument guide portal(s) 2412 and the insufflation port 2430, etc.

The device is designed to distract the skin and subcutaneous fat in the location where the suture is being placed thus maximizing fascial tissue capture and minimizing capture of subcutaneous fat. As illustrated in FIG. 21, when the material 2065 is body tissue, then the defect can be a hole 2060 in the body tissue resulting from removal of a laparoscopic trocar from the body tissue. The hole 2060 may extend through multiple layers of body tissue (e.g., skin and fascia), where the inner surface 2067 refers to the fascia surface below the skin that is facing the abdominal cavity. The elliptical closure guide has a notch cut-out 2046 on one side (e.g., at around the midpoint) into which the fascial tissue to be sutured is captured. The fascial closure device has two guide holes, one for directing the needle (e.g., the needle guide portal 2032) and one as a suture guide (e.g., the suture guide input portal 2042). The needle guide can be oriented to capture the maximum amount of tissue (e.g., at greater than 90 degrees) and can end bluntly in a pocket (e.g., the second sub path 2062) at the tip of the closure guide device. This pocket ensures that the needle is not free in the abdominal cavity and cannot injure organs or tissue within the abdominal cavity. The suture guide cavity 2040 has a curved channel to smoothly direct the suture through the plastic guide and further direct the suture through the eye of the needle. This avoids the need to capture the suture within the abdominal cavity. The guide structure 2020 has a handle 2010 to enhance tissue manipulation and improve tissue capture.

While various embodiments have been described in relation to suturing device 2000, the features described in relation to suturing device 2000 can be implemented in other embodiments. For example, various embodiments of the suturing device described in relation to FIGS. 1-18 illustrate various implementations of certain features shown and described with reference to suturing device 2000. For example, the elongated handle 50 (e.g., FIG. 2) can be a handle structure, such as handle structure 2010 shown in FIG. 20. Further, in various embodiments, the base 10 and elongated handle 50 (e.g., FIG. 3) can extend primarily along a first vector, such as a vector oriented parallel to the top surface of the elongated handle 50, between a first coupling region and a handle region. In this regard, the base 10 (e.g., FIG. 3) can be an implementation of the first coupling region, such as first coupling region 2012 shown in FIG. 20, and the elongated handle 50 can be an implementation of the handle region 2014 shown in FIG. 20. The elliptical cone 80 can be a guide structure extending primarily along a second vector between a second coupling region and a distraction region, such as guide structure 2020 shown in the embodiment of FIG. 20. In this regard, the second vector extends between a base 10, which in this embodiment can be an implementation of a second coupling region. The apex 20 can be an implementation of the distraction region. In relation to this embodiment, the base 10 can be considered to encompass both the first coupling region and the second coupling region. The notch 40, shown in embodiments described in FIGS. 1-18, can be considered a material capture region, such as material capture region 2026. As such, the notch 40 (e.g., material capture region) is located between the second coupling region (e.g., base 10) and the distraction region (e.g., apex 20). The embodiments shown in FIGS. 1-18 include a needle guide cavity such as the needle guide cavity 24 shown in FIG. 2. The needle guide cavity 24 extends along needle path that originates in a needle guide portal 22 in the first coupling region (e.g., base 10) and passes only partially through the guide structure (e.g., elliptical cone 80). The needle guide cavity 24 is interrupted by the capture region (e.g., notch 40). The embodiments shown in FIGS. 1-18 also include a suture guide cavity such as the suture guide cavity 34 shown in FIG. 2. The suture guide cavity 34 extends along a suture path that originates at a suture guide input portal, such as suture guide portal 32, in the first coupling region (e.g., base 10) and terminates at a suture guide exit portal, such as exit portal 26, in the capture region (e.g., notch 40).

In some embodiments, the means for capturing can include means for manually orienting the means for capturing with respect to a selected one of a plurality of penetration locations in the material 2065 surrounding the hole 2060. For example, FIGS. 1, 14, and 20 show different types of handles and other structures that can permit a surgeon or other user to manually orient the means for capturing. The handles can be implemented in any suitable manner with any suitable shape. Further, the handle can include other structural features to aid in their manual orientation function, such as ergonomic features to interface with one or more fingers and/or other hand anatomy, rubberized grips, tapering or rounding, etc. Further, the means for manually orienting can be separate from, or integrated with, other features of the means for capturing in any suitable manner. For example, rather than having a separate handle structure, a guide region of a suturing device can be elongated and/or can comprise various features that comprise means for manually orienting the means for capturing. In such an implementation, the means for orienting may include more or fewer of the various openings described with respect to various implementations of suturing devices herein (e.g., suture guide port opening, needle guide port opening, etc.).

In some embodiments, the means for capturing can include means for guiding a tip and an eye of a needle through the material at the selected penetration location, thereby shielding the tip of the needle from contact external to the means for capturing. For example, FIGS. 3, 14, and 21 show different types of needle guide cavities and other structures that can permit a surgeon or other user to guide the tip of a needle through material located within the means for capturing. The needle guide can be implemented in any suitable manner with any suitable shape. For example, if the needle is circular in shape, then the needle guide can have a circular cross-section to adapt to the shape of the needle. However, in other embodiments the needle may have an elongated or oval profile, yet the needle guide may still be circular in cross-section. In both these embodiments, the needle can rotate within the needle guide. In other embodiments, the needle and the needle guide can have profiles that align the needle within the needle guide in a specific orientation. For example both the needle and needle guide may have an oval profile, and thus, the needle will only align within the needle guide in specific orientations. Further, the means for manually orienting can be separate from, or integrate with, other features of the means for capturing in any suitable manner.

In some embodiments, the means for capturing can include means for guiding a tip of a suture through the hole 2060 and through the eye of the needle. For example, FIGS. 3, 14, and 21 show different types of suture guide cavities and other structures that can permit a surgeon or user to guide the tip of a suture through the eye of a needle. The suture guide can be implemented in any suitable manner with any suitable shape. For example, the suture guide cavity can include other structural features to aid in the guiding function, such as a suture input portal, tapering, rounding, etc. Further, the means for guiding a suture through the hole 2060 and through the eye of the needle, can be separate from, or integrated with, other features of the means for capturing in any suitable manner. For example, rather than having a separate suture guide cavity, the suture guide cavity could be combined with an insufflation port, and/or could use pressured gas to advance and guide the suture through the hole 2060 and eye of the needle. In such an implementation, the means for guiding may include more or fewer of the openings described with respect to various implementations of suturing devices herein (e.g., suture guide port opening, needle guide port opening, etc.).

Figure 25A:
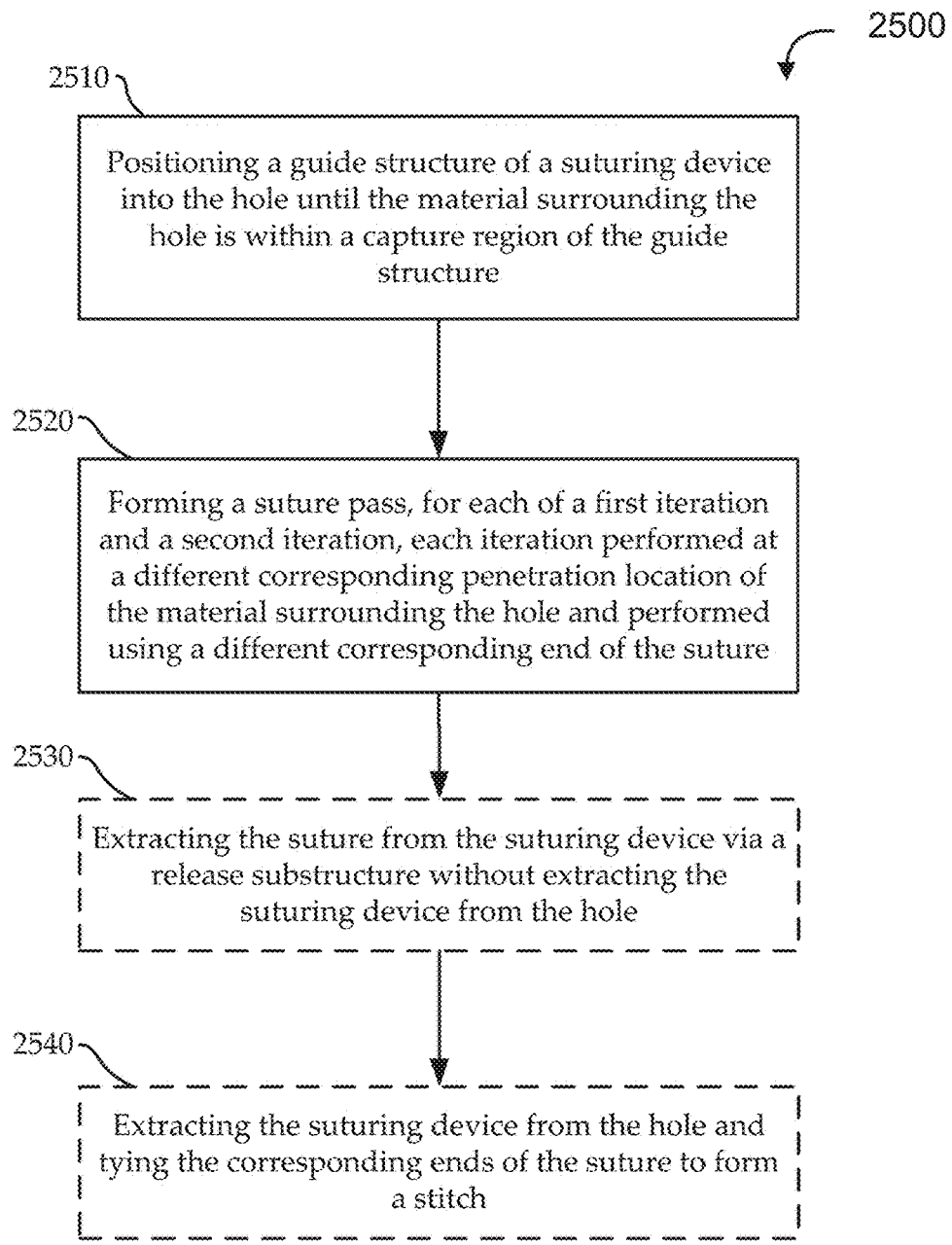
FIGS. 25A and B show a flow diagram of a method of suturing a hole with a suturing device, in an embodiment of the disclosed technology.
Figure 25B:
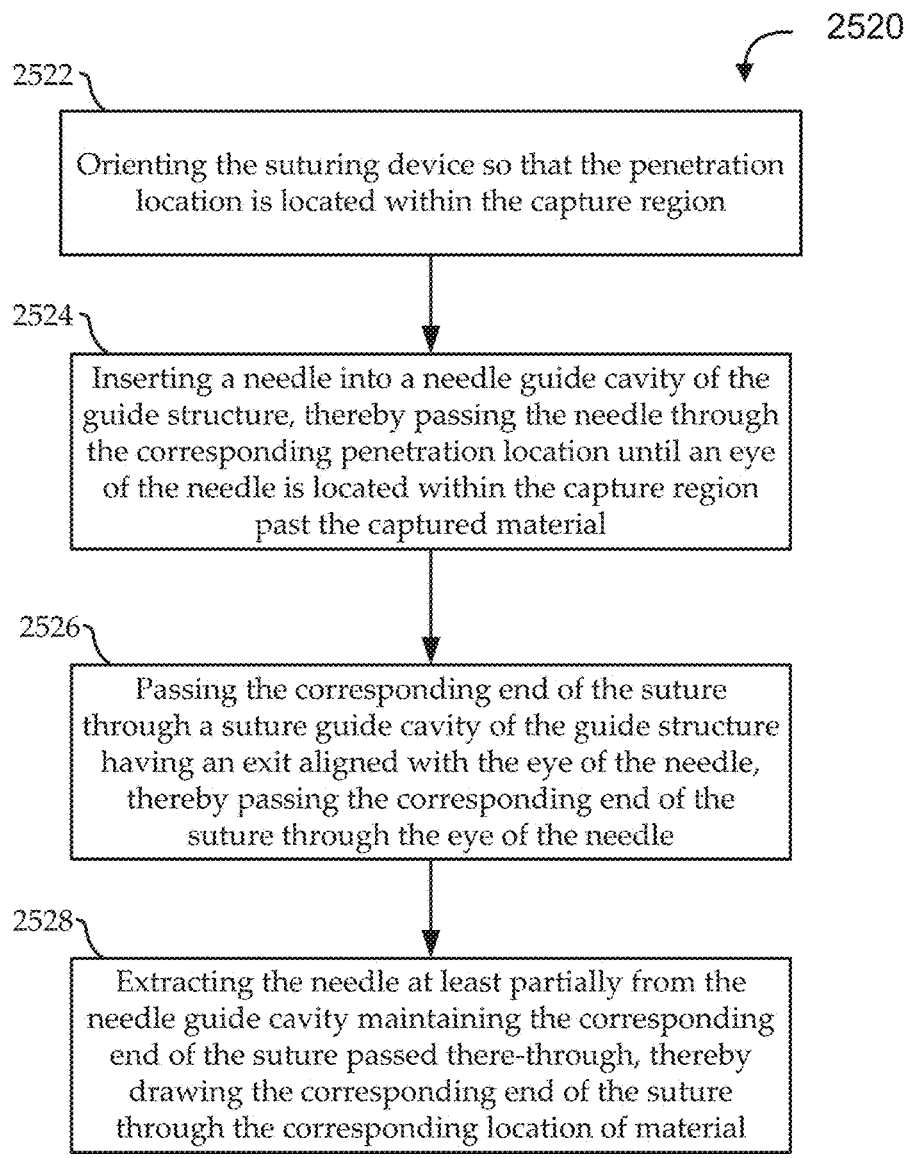

FIGS. 25A and 25B show a flow diagram for a method 2500 of using a fascial closure device to suture fascia in a laparoscopy port, according to various embodiments. For added clarity, various stages of the method 2500 are illustrated in, and described with reference to, FIGS. 26A-26I. Though FIGS. 26A-26I illustrate use of the suturing device 2000 of FIG. 20, embodiments of the method 2500 can be implemented with any suitable suturing device, including any of the suturing device embodiments described with reference to FIGS. 1-24 above.

Figure 26A:
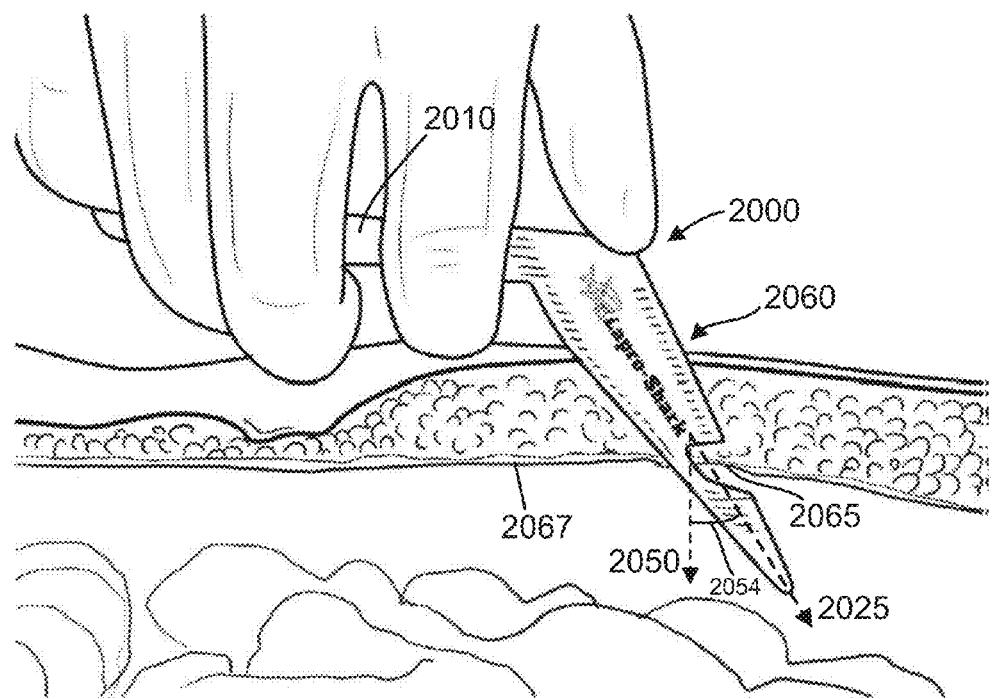
FIGS. 26A-26I show a sequence of illustrations of the method shown in FIG. 25, in an embodiment of the disclosed technology.
Figure 26B:
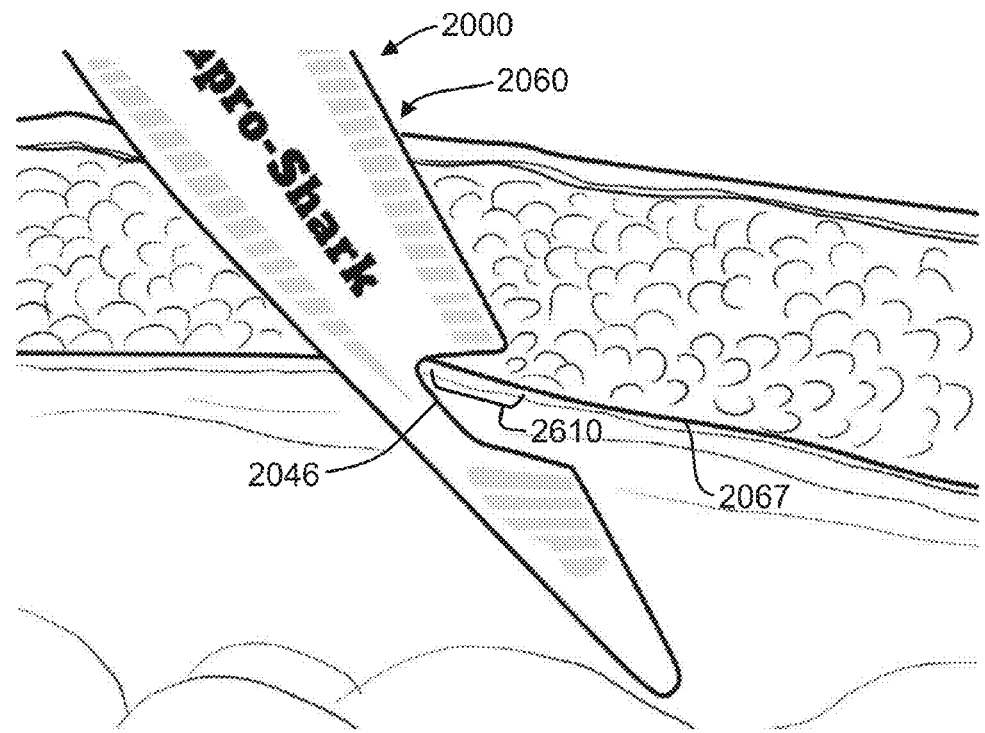

Turning first to FIG. 25A, a first portion of the method 2500 is shown. Some embodiments of the method 2500 begins at stage 2510 by positioning a guide structure of a suturing device into a hole until material surrounding the hole is within a capture region of the guide structure. For example, at the conclusion of a laparoscopy procedure, a trocar can be removed and replaced with the fascial closure device 2000. As illustrated in FIG. 26A, the implementations include positioning a guide structure of a suturing device into the hole 2060 until material 2065 surrounding the hole 2060 is within a capture region of the guide structure. In certain embodiments, the positioning is along a distraction vector 2025 to distract multi-layered material around the hole 2060. The hole 2060 defines a hole vector 2050 that passes into the hole 2060 and is substantially normal to an inner surface 2067 of the material 2065 adjacent to the hole 2060, and the hole vector 2050 and the distraction vector 2025 form an acute angle 2054. For example, a surgeon holding the handle 2010 of the suturing device 2000 substantially parallel to the outer surface of the defect can push the guide structure into the defect substantially along the direction 2025, such that the distraction region distracts layers of fat and tissue as the suturing device enters the defect. As shown in FIG. 26B, the suturing device 2000 can be advanced through the defect created by the trocar (e.g., a "port") to ensure that the cut-out notch 2046 of the suturing device 2000 is below the inner surface 2067 of the defect 2060 (e.g., skin and subcutaneous fat). The suturing device 2000 can be manipulated (e.g., by exerting pressure and/or otherwise manipulating the handle 2010) to capture a desired amount of fascia 2610 (e.g., a defined maximal amount, such as 1 cm) into the cut-out notch 2046.

Stage 2520 proceeds by forming a suture pass, for each of a first iteration and a second iteration, where each iteration is performed at a different corresponding penetration location of material 2065 surrounding the hole 2060 and performed using a different corresponding end of the suture. In some embodiments, each iteration of stage 2520 is performed according to stages 2522-2528. More specifically, stage 2520 comprises a series of sub-stages shown in FIG. 25B. Stage 2522 comprises orienting the suturing device 2000 so that the penetration location is located within the capture region. For example, FIG. 26B shows the suturing device 2000 having its guide structure 2020 positioned within hole 2060. The user can manipulate the handle of the device 2000 until a desired amount of fascia 2610 is located within the capture region 2026. In some situations, it may be hard if not impossible for the user to observe when the desired amount of fascia 2610 is positioned within the material capture region 2026. As described above, the orientation of the handle 2010 in relation to the guide structure 2020 can help a user position the device 2000. Specifically, in certain embodiments, the direction of the first vector 2015 is parallel to the outer capture feature 2052. Thus, the user can use the position of the handle relative to the hole 2060 to determine the orientation of the outer capture feature 2052 in relation to the inner surface 2067 of material 2065. In one embodiment the user can position the first vector 2015 of the handle 2010 to be substantially parallel to the inner surface 2067 of the hole 2060. In this orientation, the second vector 2025 of the guide structure 2020 will be located at an acute angle 2054 relative to the hole axis 2050. Stated otherwise, the guide structure will be oriented in the hole 2060 at an angle, and the outer capture feature 2052 will be substantially parallel to the inner surface 2067. Orienting the device 2000 in such away helps the user capture the desired amount of fascia 2610 without the user needing to directly observe the fascia 2610 positioned within the material capture region 2026.

Figure 26C:
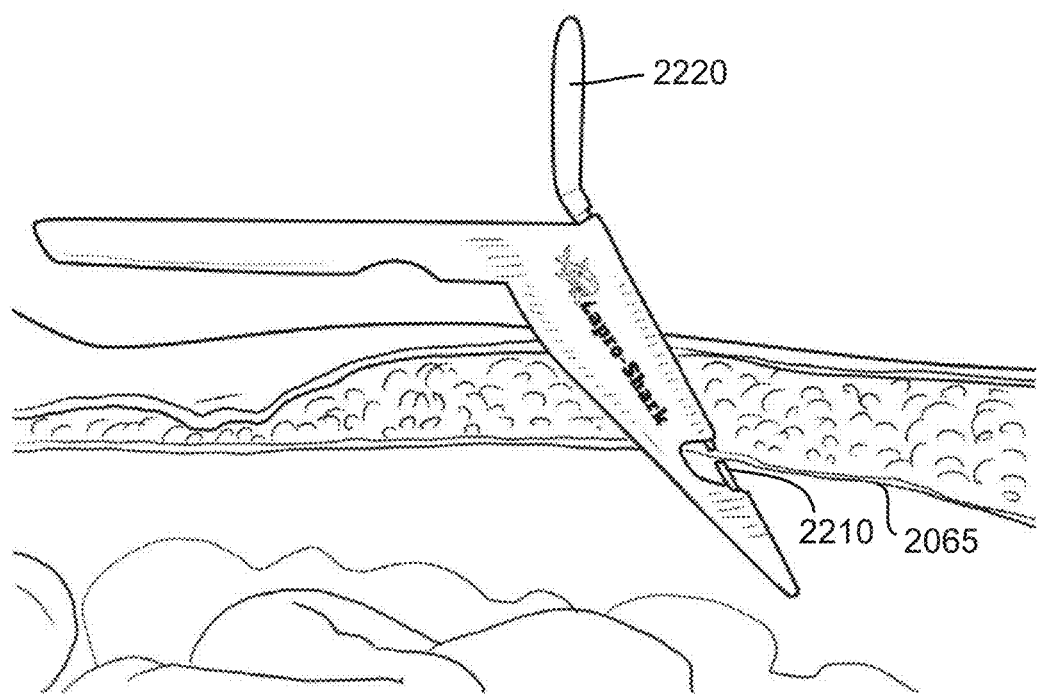

Stage 2524 proceeds by inserting a needle into a needle guide cavity of the guide structure, thereby passing the needle through the corresponding penetration location until the eye of the needle is located within the capture region past the captured material. For example, as illustrated in FIG. 26C, the needle can be introduced through the needle guide cavity 2030, driving the needle through the material 2065 (e.g., tissue), and coming to rest in the second sub path 2062 (FIG. 21) in the capture region of the device 2000. A novel interface between the needle handle 2220 and the needle guide cavity 2030 can help ensure that the needle handle 2220 is completely seated in the needle guide cavity 2030, while also ensuring that the eye 2230 of the needle is oriented to open in the direction of the suture guide 2040.

Figure 26D:
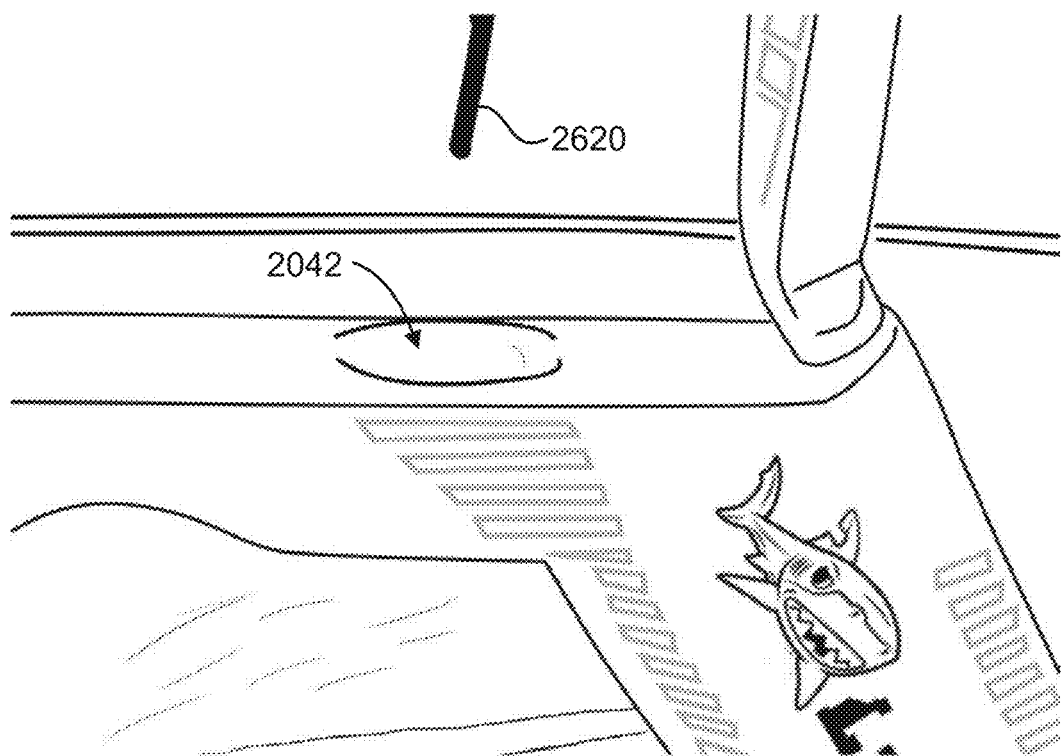
Figure 26E:
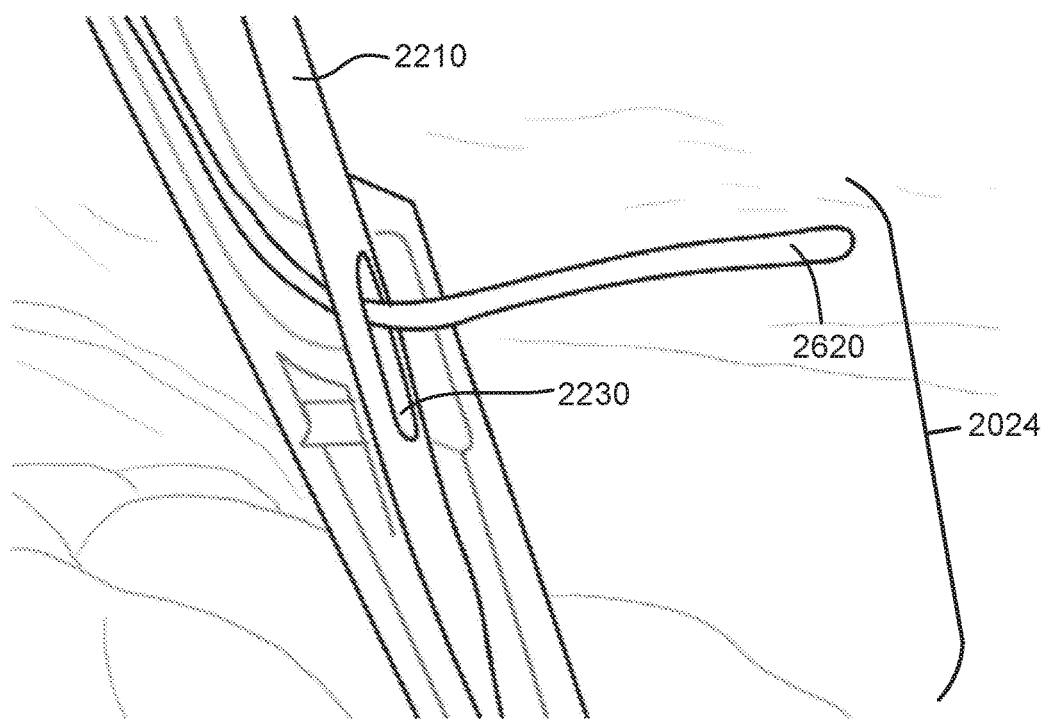

At stage 2526, embodiments include passing the corresponding end of the suture through a suture guide cavity of the guide structure having an exit aligned with the eye of the needle, thereby passing the corresponding end of the suture through the eye of the needle. For example, as illustrated in FIGS. 26D and 26E, the suture guide is oriented in such a way as to direct the suture down the device, through the eye of the needle, and out of the suturing device 2000 (e.g., exiting the device in a direction substantially parallel to the plane of the fascia).

Figure 26F:
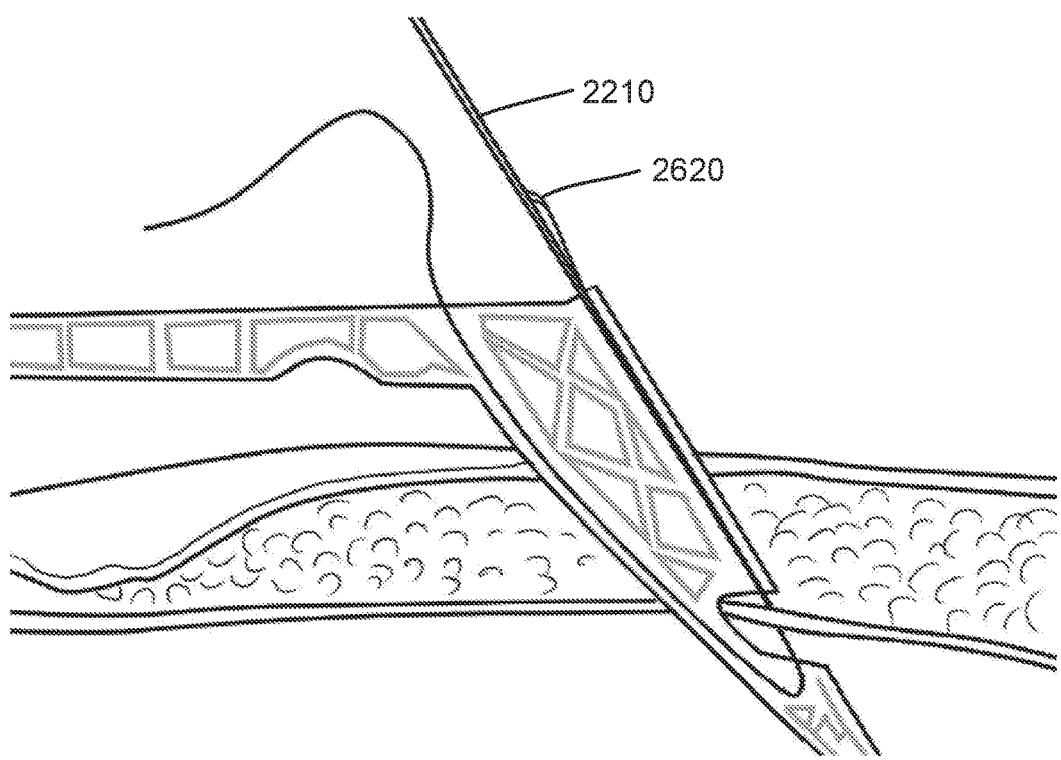

At stage 2528, embodiments include extracting the needle at least partially from the needle guide cavity, maintaining the corresponding end of the suture passed there-through, thereby drawing the corresponding end of the suture through the eye of the needle. For example, as illustrated in FIG. 26F, when the needle 2210 is pulled upward from the needle guide cavity 2030, the end of the suture 2620 passed through the eye 2230 is captured between the needle 2210 and the inside wall of the needle guide cavity 2030. As the needle 2210 is retracted from the needle guide cavity 2030, the suture 2620 is pulled through the material 2065 and subsequently the needle guide cavity 2030. Thus, extracting the needle from the suturing device 2000 can pull the suture 2620 through the tissue. The needle guide cavity 2030 can be sized so that the suture 2620 is effectively bent over and held in place within the eye of the needle as the needle is extracted from the device.

Although, embodiments of the suturing method have described by inserting the needle at step 2524 and then passing the corresponding end of the suture through the eye of the needle at stage 2526, the method steps are not required to be performed in this particular order. For example, stage 2526 could precede stage 2524. In various embodiments, passing the corresponding end of the suture through the suture guide cavity 2030 of the guide structure 2020 having an exit aligned with the eye of the needle 2230 thereby passing the corresponding end of the suture through the eye 2230 of the needle 2210, can include inserting the corresponding end of the suture 2620 into the suture guide cavity 2030 before the needle 2210 is inserted into the needle guide cavity 2040. Then, inserting the needle 2210 into the needle guide cavity 2040 of the guide structure 2020, thereby passing the needle 2210 through the corresponding penetration location until an eye 2230 of the needle 2210 is located within the capture region past the captured material, includes the needle 2210 being passed by the end of suture already positioned at least partially within the needle guide cavity 2040. That is, the eye 2230 of the needle 2210 can be open and/or have a grasping feature that slides past the end of suture when the needle 2210 is being inserted. Once the eye 2230 of the needle 2210 and/or grasping feature has passed the suture 2620, the suture 2620 is captured by the eye and/or grasping feature. Now, the end of suture 2620 is positioned within the eye 2230 of the needle 2210 and/or grasping feature and both the suture 2620 and eye 2230 of the needle 2210 are located below the penetration location. At stage 2528, extracting the needle 2210 at least partially from the needle guide cavity 2040 maintaining the corresponding end of the suture 2620 passed there-through, thereby drawing the corresponding end of the suture 2620 through the corresponding location of material 2067, includes the suture 2620, which is captured in the open eye 2230 structure of the needle and/or grasping feature, being pulled by the eye 2230 of the needle 2210 and/or grasping feature through the penetration location.

Figure 26G:
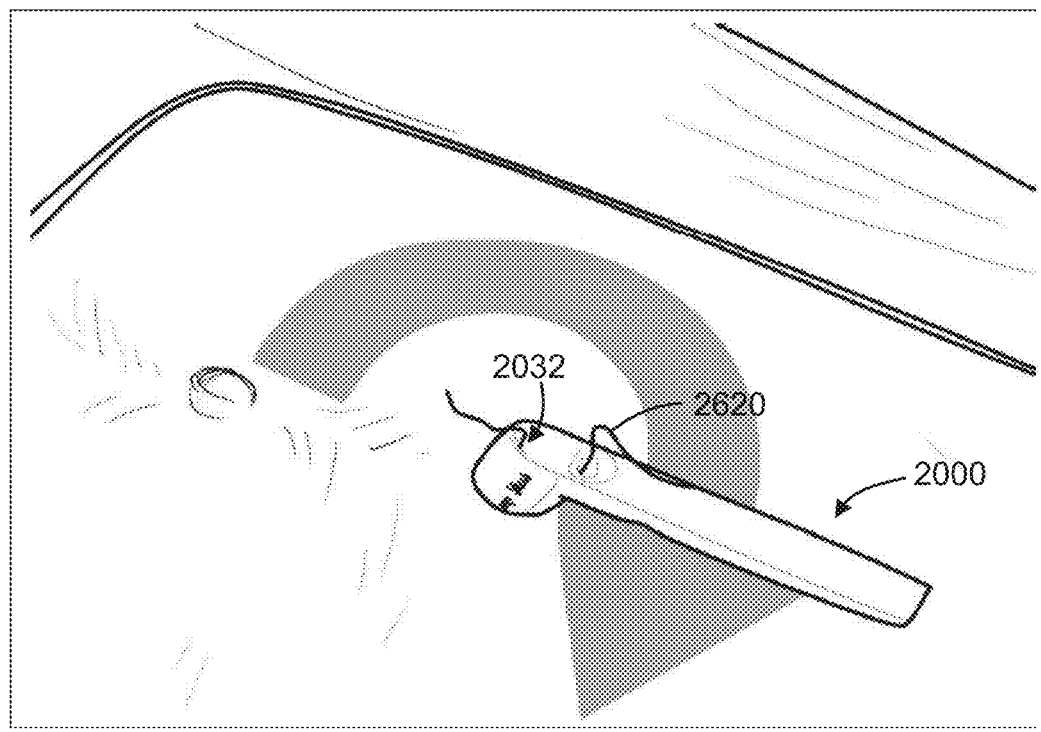
Figure 26H:
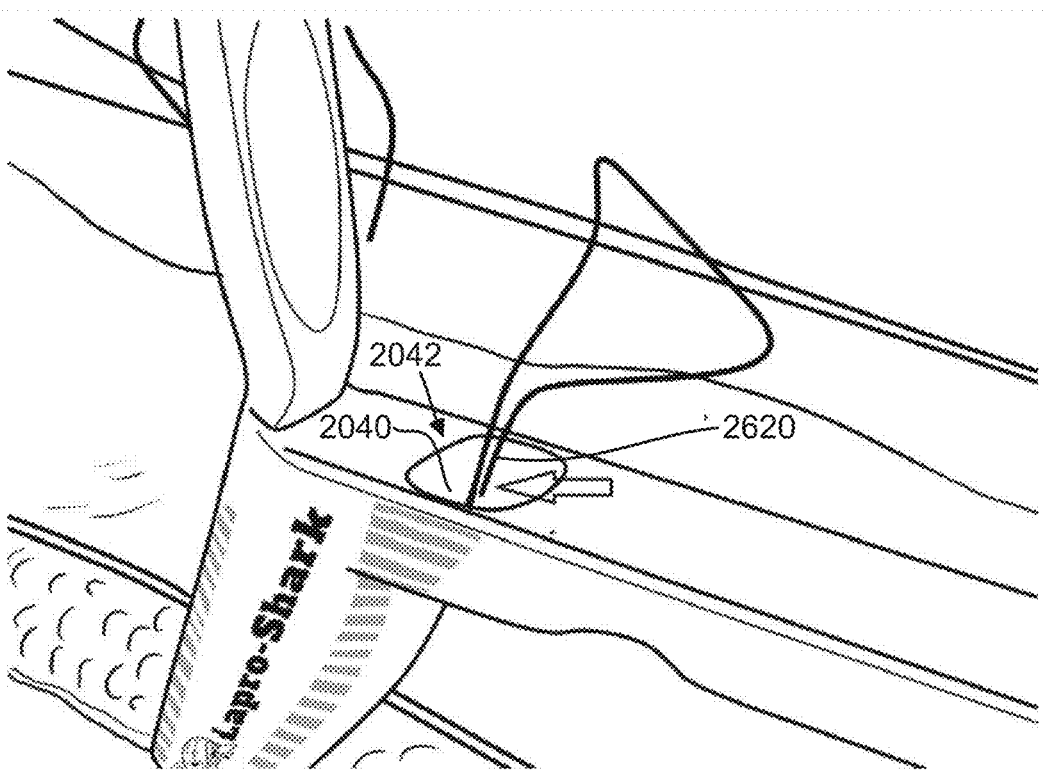
Figure 26I:
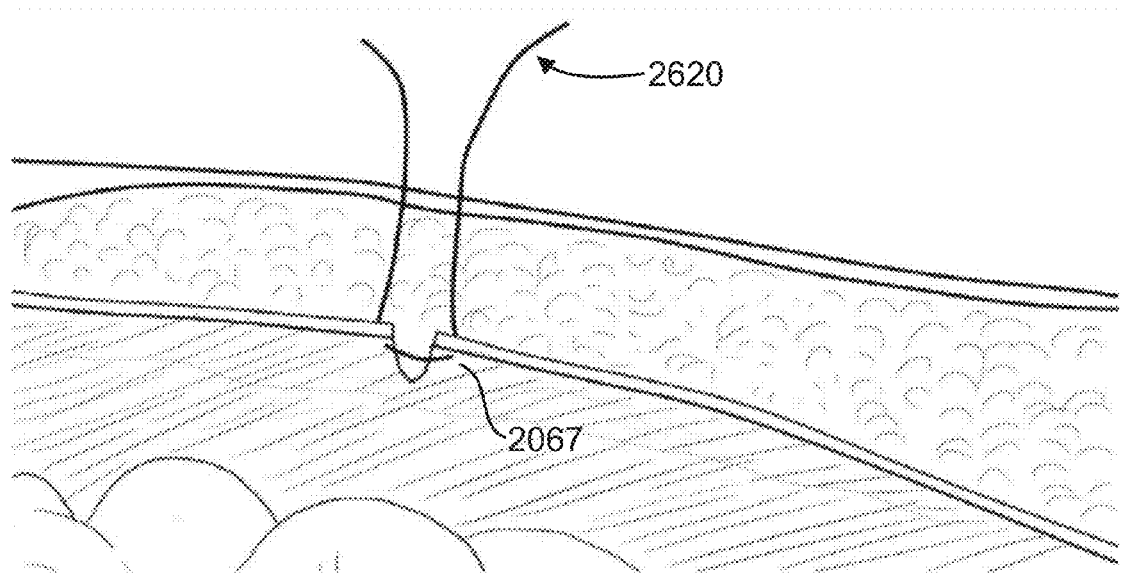

As described above, stage 2520 can include forming a suture pass for each of a first and a second iteration. For example, stages 2522-2528 can be performed for a first suture pass iteration with the suturing device 2000 oriented in a first position within the defect. After completing the first pass, as illustrated in FIG. 26G, the suturing device can be rotated (e.g., 180 degrees) to capture a different portion (e.g., the opposite side) of the defect's fascia into the notch on the device. Stages 2510-2528 can be repeated with the suturing device 2000 in the second orientation to perform the second suture pass iteration. In some embodiments, the other end of the same suture 2620 can be passed through the same suture guide of the device to facilitate formation of a "U" type suture. For example, FIG. 26H illustrates the second end of the suture 2620 being passed into the suture guide cavity of the suturing device. After passing the second end of the suture 2620 into the suture guide cavity 2040 of the suturing device 2000 and through the needle 2210, the needle 2210 can be extracted from the needle guide cavity 2030, and the suturing device 2000 can be removed from the hole 2060. As illustrated in FIG. 26I, after removing the suturing device 2000 from the hole 2060, a "U" type suture remains through full a thickness of fascia in two locations (e.g., on either side) of the defect.

Some implementations of the method 2500 can include additional stages. For example, stage 2530, can include extracting the suture from the suturing device via a release substructure without extracting the suturing device from the hole 2060. For example, multiple sutures can be placed in a defect without removing the suturing device from the defect. In one embodiment, extracting the suture is accomplished through a release substructure 2310 containing a suture passage 2312 as described above with reference to FIG. 23. Further, in some embodiments, the method 2500 can continue at stage 2540 by extracting the suturing device from the hole 2060 and tying the corresponding ends of the suture to form a stitch. For example, once the desired number of sutures is placed in the defect, the suturing device 2300 can be removed from the hole 2060, and the suture can be tied (e.g., in a typical surgical fashion), thereby closing the defect.

Embodiments of the fascial closure device and/or methods of using such a device can provide various features. Some such features relate to the novel shape of the device. As illustrated in FIGS. 20-26, some embodiments of the suturing device 2000 can be angled at greater than 90 degrees with the tip of the device pointing forward. Such an arrangement can help push skin and fat layers away without excessive pushing by the surgeon. Further, the notch can be angled substantially to correspond with the angle of the device. For example, when the handle of the device is parallel with the skin layer, the nose of the device points forward at greater than 90 degrees, and the bottom (e.g., and top) portions of the notch are oriented substantially parallel to the fascial layer. This can permit the device to capture as much fascia as possible (or at least a sufficient amount) in the notch while the fat and skin layers are being distracted.

Other such features relate to the novel arrangement of the needle. Proper and convenient operation of the fascial closure device can rely on orienting the needle so that the eye of the needle is aligned with the suture channel (so the suture easily passes through the eye of the needle). Some implementations include needles having an orientable cross-section, such as a flat or oval-shaped needle, and a correspondingly shaped needle guide channel. This can permit insertion of the needle into the needle guide channel only in an orientation that properly aligns the eye with the suture channel. Other implementations involve a novel needle handle complex. The base of the needle handle (where it interfaces with the needle) can be shaped to interface with a shape of the needle guide channel opening in such a way as to ensure that, when the needle is fully inserted into the needle guide channel, the needle eye will automatically be properly aligned. The interface shape can include any useful feature. For example, the base of the needle handle can have a D-shaped cross-section, a notch or tab, etc. Further, some embodiments of the needle handle are further arranged to avoid interfering with access to the suture channel. For example, as illustrated, the needle handle can be pointed forward, away from the suture channel.

Other such features relate to novel aspects of the suture channel itself. As illustrated, the input opening of the suture channel (where the suture is inserted) is relatively large; the output opening of the suture channel is shaped to correspond to the shape of the needle eye, but slightly smaller; and the suture channel is arcuate-shaped to smoothly guide the suture from the input opening (where the suture is substantially normal to the fascial layer) to the output opening (where the suture is substantially parallel to the fascial layer). This arrangement provides a number of features. The channel is large enough to smoothly pass two sutures, while being small enough to limit the escape of gasses (e.g., $CO_2$) from the abdominal cavity; the input opening is large enough to facilitate ease of suture insertion while wearing surgical gloves; and the output opening is shaped to ensure smooth passage of the suture through the needle eye.

Other such features relate to a novel arrangement of cutouts ("fins") in the outer body of the fascial closure device. The fins permit even cooling of the injection-molded plastic outer body and help avoid faults in the plastic. The fins are also arranged in a manner that avoids interfering with operation of the device. For example, the fins, as implemented, do not appreciably catch on the skin, fat, or fascial layers; do not provide undesirable venting of gasses from the abdominal cavity; do not interfere with sterilization of the device; do not appreciably reduce the durability of the device; etc.

Other such features relate to novel multi-suture implementations. Some embodiments include a slit in the front of the device, running from the top of the needle guide channel to the top of the notch. Such a slit can allow for removal of the suture (e.g., prior to tying) without removing the device from the laparoscopy port. This can permit multiple sutures to be sewn in one port without removing the device, thereby speeding up the suturing of larger holes, limiting the escape of gasses from the cavity, etc. In some implementations, the slit is visible in the front of the device and may or may not be further shaped (e.g., with a "V"-shaped cutout at the top) to facilitate its use. In other implementations, the slit is not normally visible, but is provided by permitting some pliability in the construction of the needle guide channel. For example, some implementations of the outer body are formed in two halves (e.g., mirror images), which are snapped together using friction-fit pins. By implementing such an outer body assembly with all friction-fit pins behind the needle guide channel, there can be pliability in the front seam of the device, effectively forming the slit.

The methods disclosed herein comprise one or more actions for achieving the described method. The method and/or actions may be interchanged with one another without departing from the scope of the claims. In other words, unless a specific order of actions is specified, the order and/or use of specific actions may be modified without departing from the scope of the claims.

Other examples and implementations are within the scope and spirit of the disclosure and appended claims. For example, features implementing functions may also be physically located at various positions, including being distributed such that portions of functions are implemented at different physial locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

Various changes, substitutions, and alterations to the techniques described herein can be made without departing from the technology of the teachings as defined by the appended claims. Moreover, the scope of the disclosure and claims is not limited to the particular aspects of the process, machine, manufacture, composition of matter, means, methods, and actions described above. Processes, machines, manufacture, compositions of matter, means, methods, or actions, presently existing or later to be developed, that perform substantially the same function or achieve substantially the same result as the corresponding aspects described herein may be utilized. Accordingly, the appended claims include within their scope such processes, machines, manufacture, compositions of matter, means, methods, or actions.

What is claimed is:

1. A suturing device for closing a hole in a material, the suturing device comprising:
   a handle structure extending primarily along a first vector between a first coupling region and a handle region;
   a guide structure extending primarily along a second vector between a second coupling region and a distraction region, the second coupling region coupled with the first coupling region, the guide structure further comprising a material capture region located between the second coupling region and the distraction region;
   a needle guide cavity, extending along a needle path that originates at a needle guide portal in the first coupling region and passes only partially through the guide structure, interrupted by the capture region; and
   a suture guide cavity, extending along a suture path that originates at a suture guide input portal in the first coupling region and terminates at a suture guide exit portal in the capture region,
   wherein the needle guide cavity comprises a needle orientation feature having an asymmetric structural feature that interfaces with a corresponding feature on a needle to rotationally guide the needle into only a single orientation when the needle is fully inserted into the needle guide cavity, the single orientation corresponding to an eye of the needle being rotationally aligned with the suture exit portal.

2. The suturing device of claim 1, wherein the second coupling region is coupled with the first coupling region to form an obtuse angle between the first vector and the second vector.

3. The suturing device of claim 1, wherein:
   the hole defines a hole axis that passes through the hole, the hole axis being substantially normal to an inner surface of the material adjacent to the hole; and
   the material capture region comprises a notch cut-out that defines an inner capture feature oriented according to the first vector, such that, when the guide structure is inserted in the hole with the handle structure located outside the hole and oriented so that the first vector is perpendicular to the hole axis, the inner capture feature is located below the inner surface and is substantially coplanar with the inner surface of the material adjacent to the hole.

4. The suturing device of claim 3, wherein:
   the notch cut-out further defines an outer capture feature positioned to be located above the inner surface when the inner capture feature is located below the inner surface; and
   the needle path comprises a first sub-path that originates at the needle guide portal and ends at an opening in the outer capture feature, and a second sub-path that originates at an opening in the inner capture feature and ends within the guide structure, the first sub-path being aligned with the second sub-path, such that the needle guide cavity is interrupted by the capture region.

5. The suturing device of claim 1, further comprising: the needle shaped according to the needle path, the needle having a needle handle, the needle eye, and a needle tip, the needle sized, so that, when the needle is inserted into the needle guide cavity, the needle handle is proximate to the needle guide portal, the needle eye is within the capture region, and the needle tip is within the distraction region.

6. A kit comprising the suturing device of claim 1, and further comprising:
   the needle shaped according to the needle path and sized, so that, when the needle is inserted into the needle guide cavity, a handle side of the needle protrudes from the needle guide portal, and a tip side of the needle is within the distraction region.

7. The suturing device of claim 1, wherein:
   the needle guide portal comprises the needle orientation feature; and
   the asymmetric structural feature is to fully interface with a corresponding feature on a handle of the needle to rotationally align the needle in only the single orientation.

8. The suturing device of claim 1, further comprising:
   a release substructure formed in the handle structure and the guide structure, the release substructure positionally corresponding to the needle guide cavity between the needle guide portal and the capture region and sized to permit passage of a suture.

9. The suturing device of claim 1, further comprising:
   an insufflation cavity that originates at an insufflation port located on the handle structure and extends to an insufflation exit port located in the guide structure.

10. The suturing device of claim 1, wherein the needle path is linear.

11. The suturing device of claim 1, wherein the handle structure and the guide structure are manufactured as a unitary structure.

12. The suturing device of claim 1, wherein the material is body tissue, and the hole is a defect in the body tissue resulting from removal of a laparoscopic trocar from the body tissue.

13. The suturing device of claim 1, wherein the second coupling region is coupled with the first coupling region, such that the handle structure is removable from the guide structure.

14. A suturing device for closing a hole in a material, the suturing device comprising:
   a handle structure extending primarily along a first vector between a first coupling region and a handle region;
   a guide structure extending primarily along a second vector between a second coupling region and a distraction region, the second coupling region coupled with the first coupling region, the guide structure further comprising a material capture region located between the second coupling region and the distraction region;
   a needle guide cavity, extending along a needle path that originates at a needle guide portal in the first coupling region and passes only partially through the guide structure, interrupted by the capture region;
   a suture guide cavity, extending along a suture path that originates at a suture guide input portal in the first coupling region and terminates at a suture guide exit portal in the capture region; and
   an instrument guide passage extending along an instrument path that originates at an instrument guide portal in the first coupling region and extends to an instrument exit portal that defines an instrument cavity located within the distraction region, wherein the distraction region proximate to the instrument cavity comprises a window and a mirror oriented, such that a suture exiting the suture guide exit portal is visible to a camera located in the instrument cavity via the mirror and the window.

15. The suturing device of claim 14, wherein the instrument cavity comprises an access door that is openable to advance a laparoscopic instrument into a region below the capture region.

16. The suturing device of claim 14, further comprising: an insufflation cavity that originates at an insufflation port located on the handle structure and extends to an insufflation exit port located in the guide structure.

17. A suturing device for closing a hole in a material, the suturing device comprising:

a handle structure extending primarily along a first vector between a first coupling region and a handle region;

a guide structure extending primarily along a second vector between a second coupling region and a distraction region, the second coupling region coupled with the first coupling region, the guide structure further comprising a material capture region located between the second coupling region and the distraction region;

a needle guide cavity, extending along a needle path that originates at a needle guide portal in the first coupling region and passes only partially through the guide structure, interrupted by the capture region;

a suture guide cavity, extending along a suture path that originates at a suture guide input portal in the first coupling region and terminates at a suture guide exit portal in the capture region; and a release substructure formed in the handle structure and the guide structure, the release substructure positionally corresponding to a suture passage along a wall of the needle guide cavity between the needle guide portal and the capture region sized to permit passage of a suture from within the needle guide cavity to outside the suturing device through the suture passage.

18. The suturing device of claim 17, further comprising: an insufflation cavity that originates at an insufflation port located on the handle structure and extends to an insufflation exit port located in the guide structure, wherein the insufflation cavity is separate from the release substructure, such that gas passing through the insufflation cavity does not escape through the release substructure.

19. The suturing device of claim 17, wherein the needle path is linear and asymmetric.

* * * * *